United States Patent [19]

Banes

[11] Patent Number: 5,593,891
[45] Date of Patent: Jan. 14, 1997

[54] CULTURE PLATE WITH SPLASH GUARD

[76] Inventor: Albert J. Banes, 1821 Coleman Loop Rd., Hillsborough, N.C. 27278

[21] Appl. No.: 337,261

[22] Filed: Nov. 10, 1994

[51] Int. Cl.$^6$ ................................................. C12M 1/22
[52] U.S. Cl. .................. 435/305.1; 435/305.4; 220/731
[58] Field of Search ................ 435/288.3, 305.1–305.4, 435/283.1; 422/102, 99; 220/695, 698, 702, 719, 731

[56] References Cited

U.S. PATENT DOCUMENTS

| | | | |
|---|---|---|---|
| 3,248,302 | 4/1966 | Mackin | 195/139 |
| 3,677,904 | 7/1972 | Fitzgerald | 195/103.5 |
| 3,751,341 | 8/1973 | Seitz et al. | 195/139 |
| 3,968,012 | 7/1976 | Jones | 435/309.1 |
| 4,130,215 | 12/1978 | Corey et al. | 220/719 |
| 4,146,157 | 3/1979 | Dixon et al. | 222/424 |
| 4,299,921 | 11/1981 | Youssef | 435/298 |
| 4,665,035 | 5/1987 | Tunac | 435/296 |
| 4,743,556 | 5/1988 | Ervin | 435/297 |
| 4,775,067 | 10/1988 | Mount | 220/1 |
| 4,801,548 | 1/1989 | Takakura et al. | 435/301 |
| 4,911,319 | 3/1990 | DeJean | 220/4 A |
| 5,021,351 | 6/1991 | Ervin | 435/297 |

FOREIGN PATENT DOCUMENTS

| | | | |
|---|---|---|---|
| 2636516 | 3/1990 | France | 220/731 |
| 0540855 | 12/1931 | Germany | 220/731 |
| 1542541 | 2/1990 | U.S.S.R. | 220/719 |
| 1428356 | 3/1976 | United Kingdom | 220/731 |

OTHER PUBLICATIONS

Baskerville. Figures only of Great Brit. Patent #24619 (Nov.–1906).

*Primary Examiner*—William H. Beisner
*Attorney, Agent, or Firm*—Webb Ziesenheim Bruening Logsdon Orkin & Hanson, P.C.

[57] ABSTRACT

Disclosed is a culture plate which includes a splash guard for directing liquid flows away from a top edge of a base sidewall and back into the base. The splash guard can be attached to either the base or a lid of the culture plate. The splash guard can include a baffle attached permanently or removably to the inner surface of the base sidewall and extending inwardly and downwardly at an angle to the base sidewall. The baffle can be integral with the base sidewall. The splash guard can also include a support bracket configured to hang on the top edge of the base sidewall, with the baffle attached to the support bracket. Also disclosed is a splash guard which can be inserted within or attached to the base of a standard culture plate.

20 Claims, 18 Drawing Sheets

CULTURE PLATE WITH SPLASH GUARD

BACKGROUND OF THE INVENTION

1. Field of the Invention

This invention relates to culture plates and, more particularly, to culture plates which have an element for preventing splashing of liquids contained therein.

2. Description of the Prior Art

The use of culture plates, traditionally known as Petri dishes or culture dishes, in growing or culturing bacteria, eucaryotic cells, or other organisms is well known. A typical culture plate is a clear plastic structure including a cylindrical, open-topped base and a complementary or mating lid configured to sit on and close off the base. Prior art patents in this field include U.S. Pat. Nos. 3,248,302; 3,677,904; 3,751,341; 4,299,921; 4,743,556; 4,801,548 and 5,021,351.

A number of culture plates are often used at one time in a batch operation. Some culture plates contain multiple wells in one device. Each culture plate will carry a desired liquid growth medium. The plates are placed on a larger tray, and the tray is moved into and out of an incubator, typically by hand. During this handling, the tray may stick in the incubator rack or may bump into the side or rear walls of the incubator and exert a jarring force on the culture plates carried by the tray. This jarring force on a tray, or even normal handling of a tray, may cause movement of the liquid media within each culture plate and result in the liquid media sloshing onto the lid or base sidewall and splashing over the top edge of the base sidewall. When liquid thus travels to the outer, non-sterile areas of the culture plate, a path is formed which permits bacteria growth to travel to the inside areas of the culture plate and to contaminate the contents therein. Clearly such contamination of an otherwise sterile culture plate is unacceptable in practice. Alternatively, media from inside the plate can splash out of the plate, down the outside sidewall and into the incubator environment. Such media leakage provides nutrients for bacteria or fungi to replicate outside the culture plate and further contaminate the otherwise clean environment inside an incubator.

Individual culture plates are also handled by a user and movement of an individual culture plate can result in the splashing of the liquid media and the same contamination problem discussed above. In addition, if the culture plate is growing or includes a pathogenic or radioactive material, or the like, it is highly undesirable for this material to splash out of the culture plate and onto the user handling the culture plate or into the incubator environment.

Therefore, it is an object of the present invention to provide a culture plate in which flows of liquid over the top of the base sidewall are eliminated or greatly reduced for all but extreme movement of the culture plate. It is another object of the present invention to provide such a fluid flow prevention feature in either a specially designed culture plate or in a modification to existing culture plates. It is a further object of the present invention to provide such a culture plate or modification in an arrangement which is reliable, easy to use, and inexpensive to manufacture.

SUMMARY OF THE INVENTION

Accordingly, I have developed a culture plate which includes a splash guard. I have also developed a splash guard which can be inserted within or attached to the base of a standard culture plate. The culture plate includes at least a base, preferably cylindrical in configuration, having a bottom wall and a sidewall extending upwardly from the bottom wall and attached thereto. The culture plate can also include a lid having a top wall and a skirt extending downwardly from the top wall and attached thereto. The lid is configured to fit over and sit on a top edge of the base sidewall and cover an inner area enclosed by the base. The splash guard is attached to either the base or the lid and extends partially inward into the inner area of the base. The splash guard is configured to direct liquid flows away from the top edge of the base sidewall and back into the base.

The splash guard can include a baffle attached to an inner surface of the base sidewall, such as an annular, ring-shaped element attached along an outer edge to the base sidewall. The baffle can extend inwardly and downwardly at an angle to the base sidewall, and can include an outer edge which is spaced from the bottom wall and sidewall of the base. Similar baffles can be attached to an inner surface of the lid top wall.

The baffle can also be removably attached to the base sidewall, such as in an insert-type of member. The splash guard can also include a support bracket configured to hang on the top edge of the base sidewall, with the baffle attached along an outer edge to the support bracket.

DESCRIPTION OF THE PREFERRED EMBODIMENTS

The present application is directed to a culture plate which includes an open-topped base and a complementary or mating lid. In accordance with the present invention, a splash guard is provided on one of the lid or the base. The splash guard extends partially inward into an inner area enclosed by the base and is configured to direct fluid flows away from a top edge of the base sidewall and back into the base. The splash guard can be embodied in many different versions and the figures herein show the various embodiments currently contemplated. The splash guard can be provided in the form of a baffle which is integral to the base sidewall, fixedly attached to the base sidewall, removably attached to the base sidewall, or attached to a support bracket which hangs on the base sidewall. In addition, the splash guard can be provided as a baffle which is attached to an inner surface of the lid top wall. The splash guard can also be provided as an insert for the base of a standard culture plate. Various modifications and variations are shown throughout the figures, but it is to be understood that one or more of these variations can be used in combinations not specifically shown in the figures. Moreover, while the figures show single well culture plates, many of the splash guard modifications can also be incorporated into each well of a multiple well culture plate. In addition, some of the embodiments may be more appropriately manufactured in accordance with certain available techniques and materials rather than other available techniques and materials.

Figure 1:
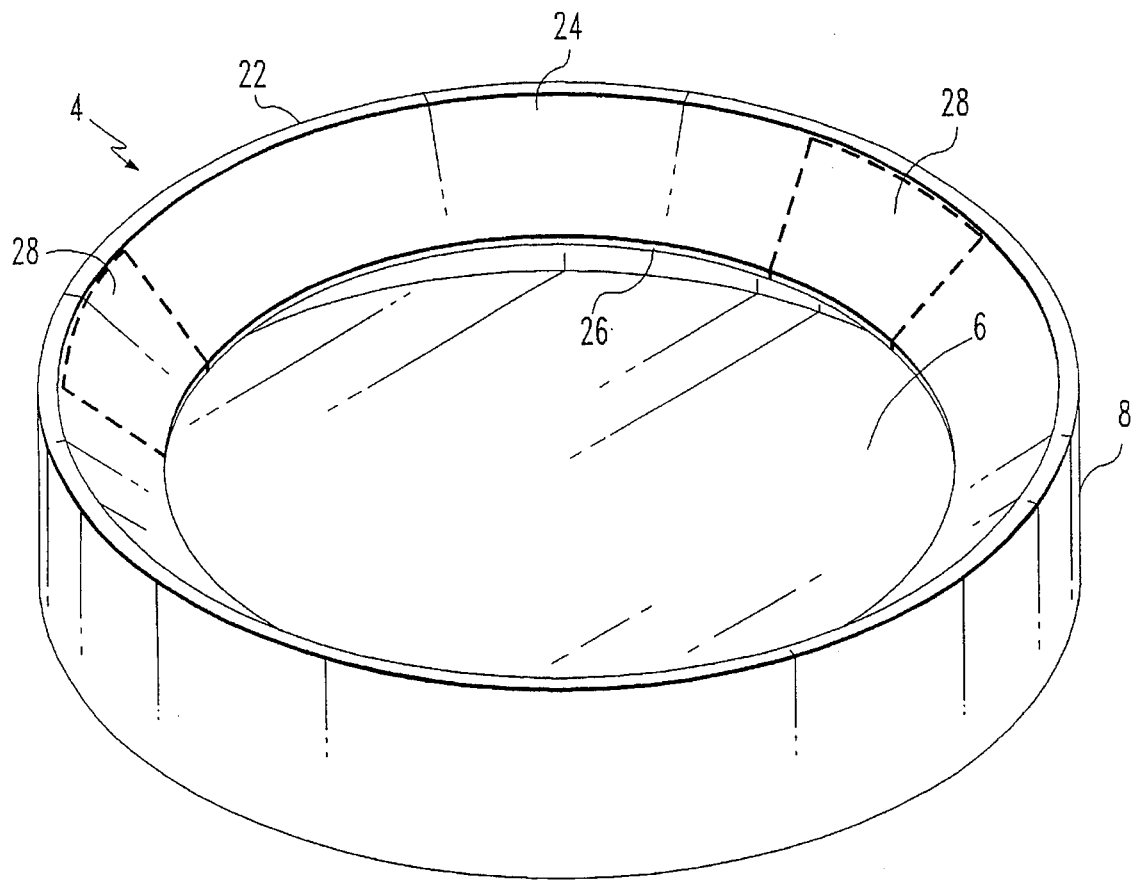
FIG. 1 is a perspective view of a base of a culture plate in accordance with the present invention.
Figure 2:
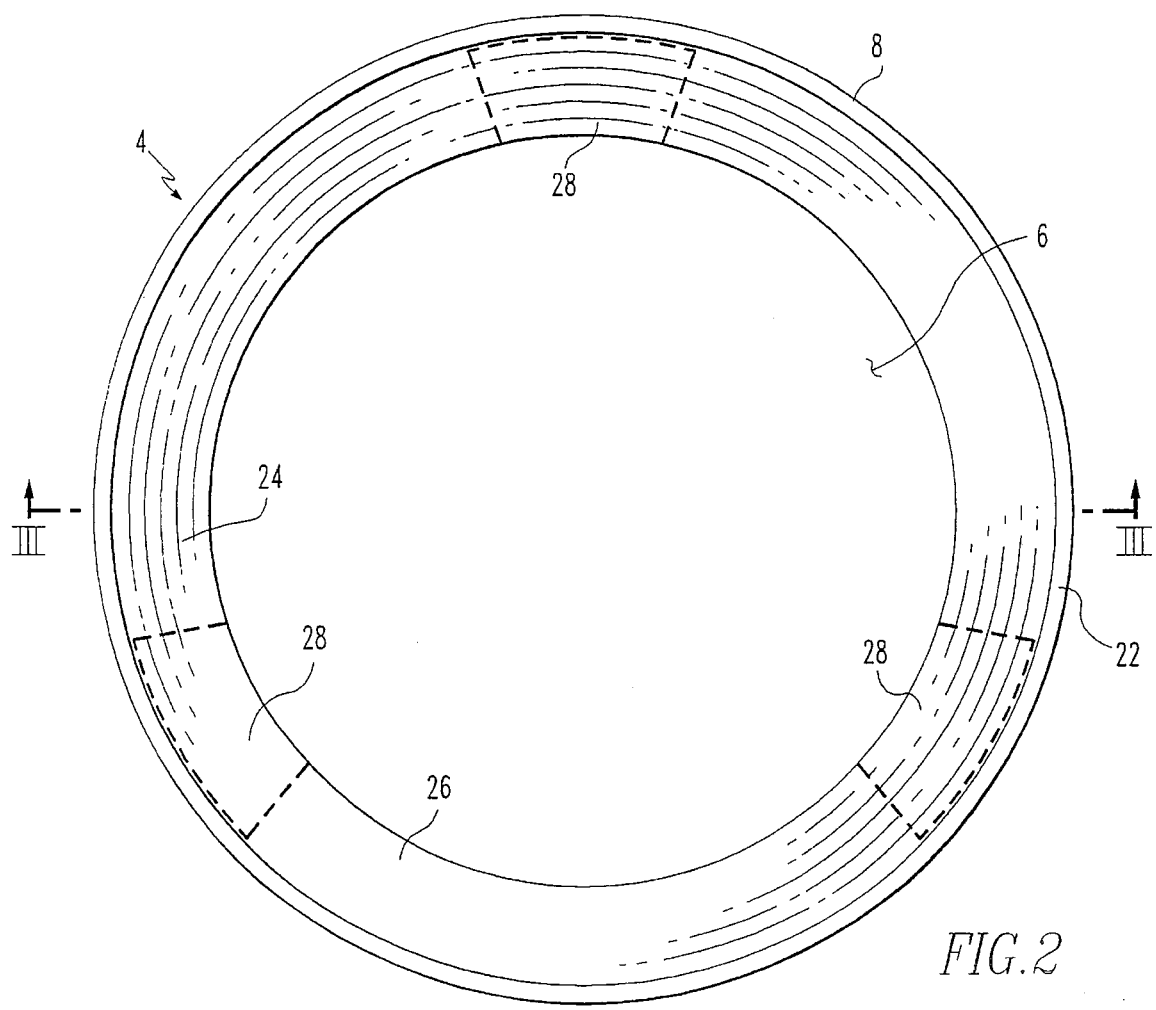
FIG. 2 is a top view of the culture plate base shown in FIG. 1.
Figure 3:
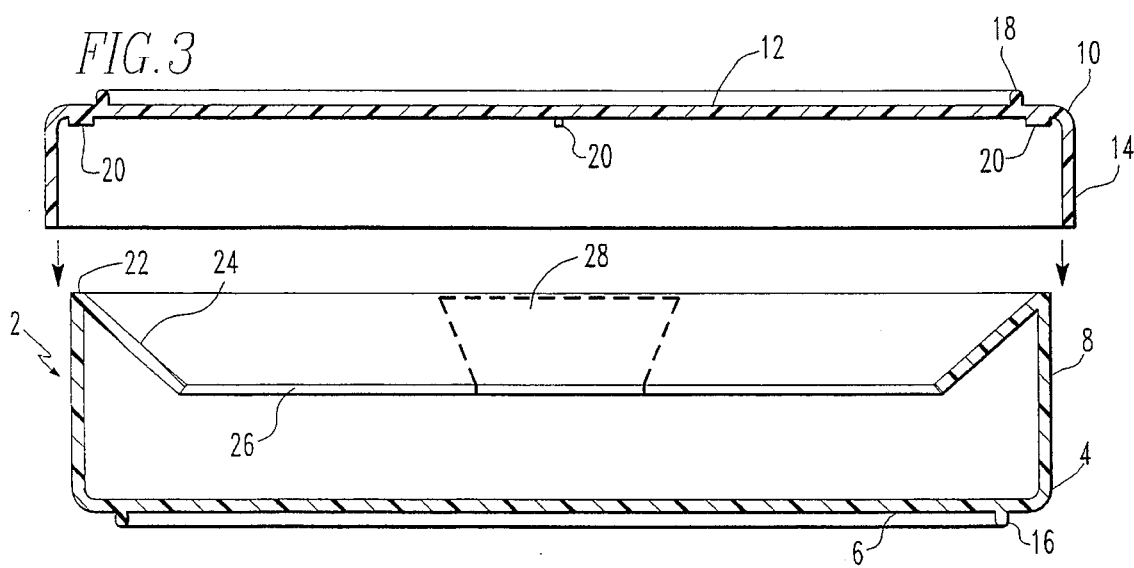
FIG. 3 is a section taken along lines III—III in FIG. 2, additionally including a lid being positioned on the base.

A first embodiment of a culture plate 2 including a splash guard in accordance with the present invention is shown in FIGS. 1–3. The culture plate includes an open-topped, cylindrical base 4 having a circular bottom wall 6 and a sidewall 8 extending upwardly around an outer peripheral edge of the bottom wall 6 and attached thereto. The culture plate 2 also includes a cylindrical lid 10 including a circular top wall 12 and a skirt 14 extending downwardly from the top wall 12 along its outer peripheral edge and attached thereto. This embodiment shows the bottom wall 6 and sidewall 8 of the base 4 formed as an integral unit, and likewise shows the top wall 12 and skirt 14 of the lid 10 formed as an integral unit. The inner or lower surface of the bottom wall 6 of the base 4 can include a circular stacking ring 16 and, likewise, the outer or upper surface of the top wall 12 of the base 4 can include a circular stacking ring 18. The outer diameter of the stacking ring 16 on the base 4 is slightly smaller than the inner diameter of the stacking ring 18 on the lid 10, however, an opposite arrangement can also be provided. The stacking rings 16, 18 cooperate with each other such that when similar culture plates 2 are stacked, the stacking rings 16, 18 nest within each other and keep the culture plates 2 from sliding horizontally. The lower or inner surface of the lid top wall 12 can include a plurality of small, separate standoffs 20 which are aligned with the top edge 22 of the base sidewall 8 and contact the base sidewall 8 when the lid 10 is positioned onto the base 4. The standoffs 20 keep the lid 10 from tightly sealing the inner area enclosed by the base 4 and allow gas flows into and out of the base 4 when the lid 10 is positioned thereon.

In accordance with the present invention, the base 4 of the culture plate 2 includes a splash guard in the form of an annular, ring-shaped baffle 24 which is connected along its outer edge to an inner surface of the base sidewall 8. In this embodiment, the baffle 24 has opposed flat surfaces and is connected along its outer edge to the base sidewall 8 near the top edge 22 thereof. The baffle 24 extends or slopes inwardly and downwardly into the interior or inner area of the base 4 and terminates in an inner edge 26 which is spaced from the bottom wall 6 and the sidewall 8 of the base 4. The baffle 24 has a sufficient width to direct liquid flows away from the top edge 22 of the base sidewall 8 and back into the base 4, yet is not too wide to occupy otherwise needed areas of the base 4 for the liquid media used during normal operation. The baffle 24 preferably extends from the base sidewall 8 at an angle of about 45°, although angles in the range of 30°–75° can be used, and angles in the range of up to and including 90° will work satisfactorily. In the embodiment shown in FIGS. 1–3, the baffle 24 has a plurality of perforated areas 28 which can be torn and removed from the baffle 24 to provide open areas therein for pouring liquids out of the base 4. Although these perforated areas 28 are not, for clarity sake, shown in any of the embodiments in the remaining figures, it is to be understood that such perforated areas 28 can be included in any of the splash guards discussed hereinafter.

Figure 4:
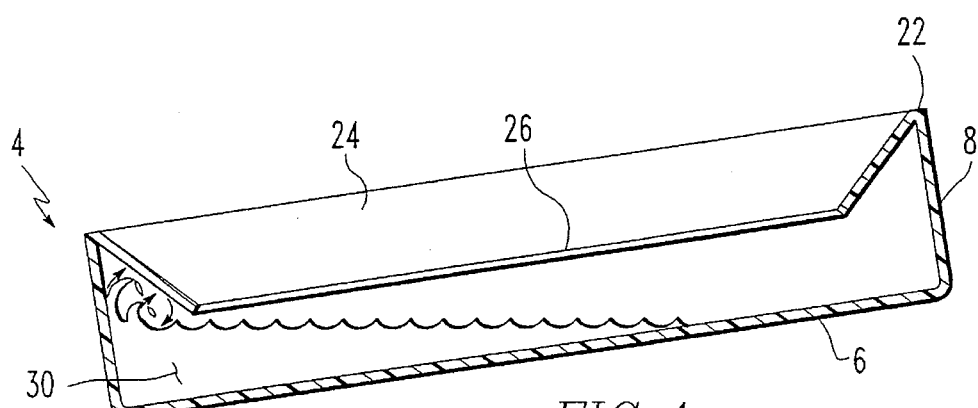
FIG. 4 is a section through the culture plate base shown in FIG. 1 and showing the operation of the splash guard.

The operation of the splash guard included in the culture plate 2 shown in FIGS. 1–3, as well as the operation of the splash guard of the present invention in general, is shown in connection with FIG. 4. Shown here is the base 4 of the culture plate 2 with a quantity of growth media in the form of a liquid 30 contained therein. If the base 4 is maintained in its normal or intended position, with the base bottom wall 6 substantially horizontal, then the liquid 30 will remain totally encased within the base 4. The liquid 30 should be well below the inner edge 26 of the baffle 24 when the base 4 is in this position. If a base 4 without a splash guard were tilted or bumped, then the liquid 30 could slosh about and splash or flow over the top edge 22 of the base sidewall 8 and contaminate the contents of the base 4. In accordance with the present invention, the splash guard, here shown as the angled baffle 24 discussed above, will intercept the flows of the liquid 30 travelling along the inner surface of the base sidewall 8 and will direct these liquid flows back into the base 4, thus preventing liquid flows over the top edge 22 of the base sidewall 8. This is illustrated clearly in FIG. 4 which shows the base 4 tilted and the liquid 30 flows extending along the inner surface of the base sidewall 8 and contacting an inner surface of the angled baffle 24.

Figure 5:
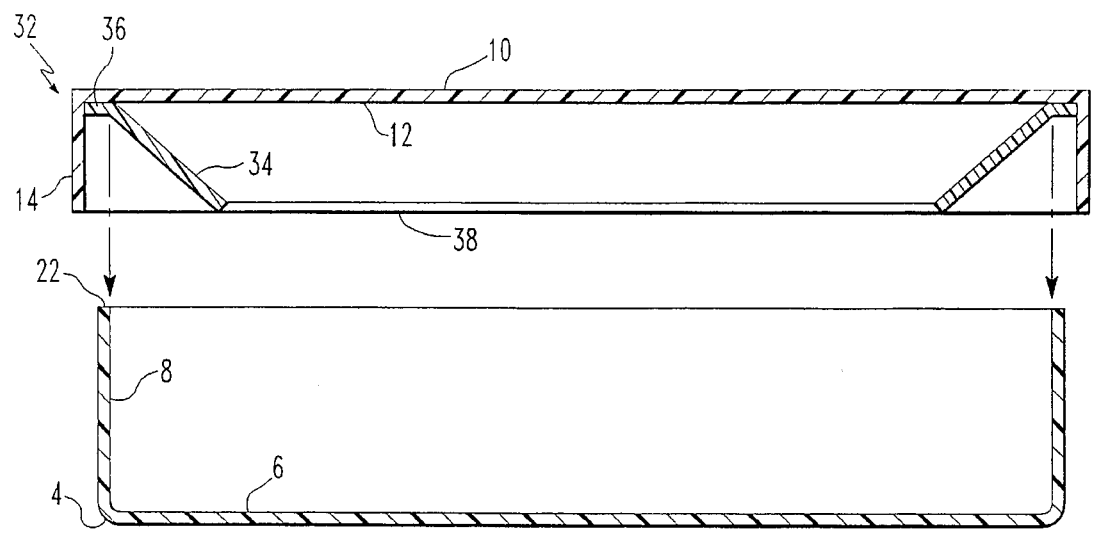
FIG. 5 is a section through another embodiment of a culture plate in accordance with the present invention showing a lid being positioned on a base.
Figure 6:
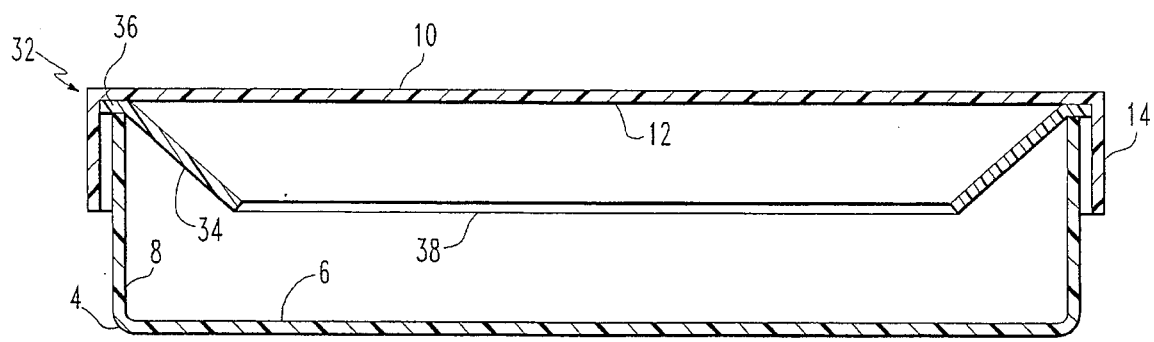
FIG. 6 is a section through the culture plate shown in FIG. 5 with the lid positioned on the base.
Figure 7:
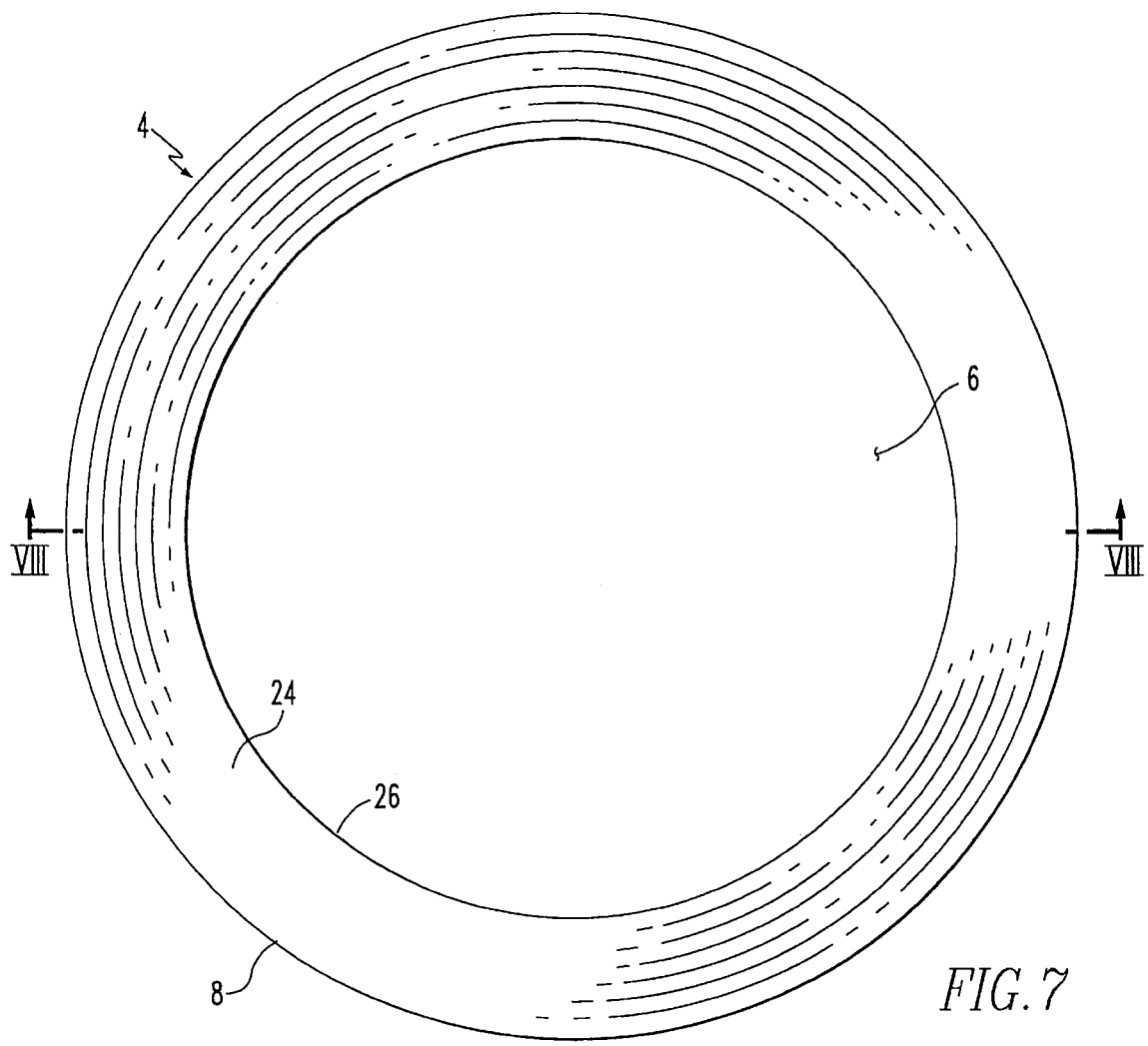
FIG. 7 is a top view of another embodiment of a culture plate base in accordance with the present invention.
Figure 8:
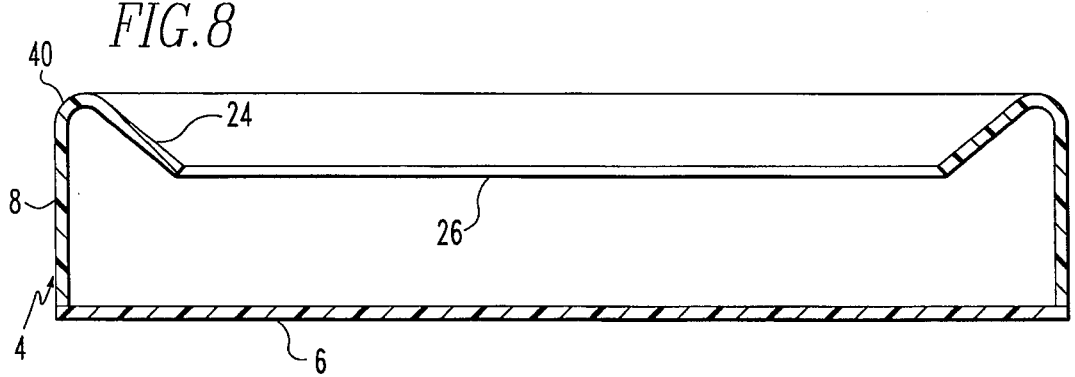
FIG. 8 is a section taken along lines VIII—VIII in FIG. 7.
Figure 9:
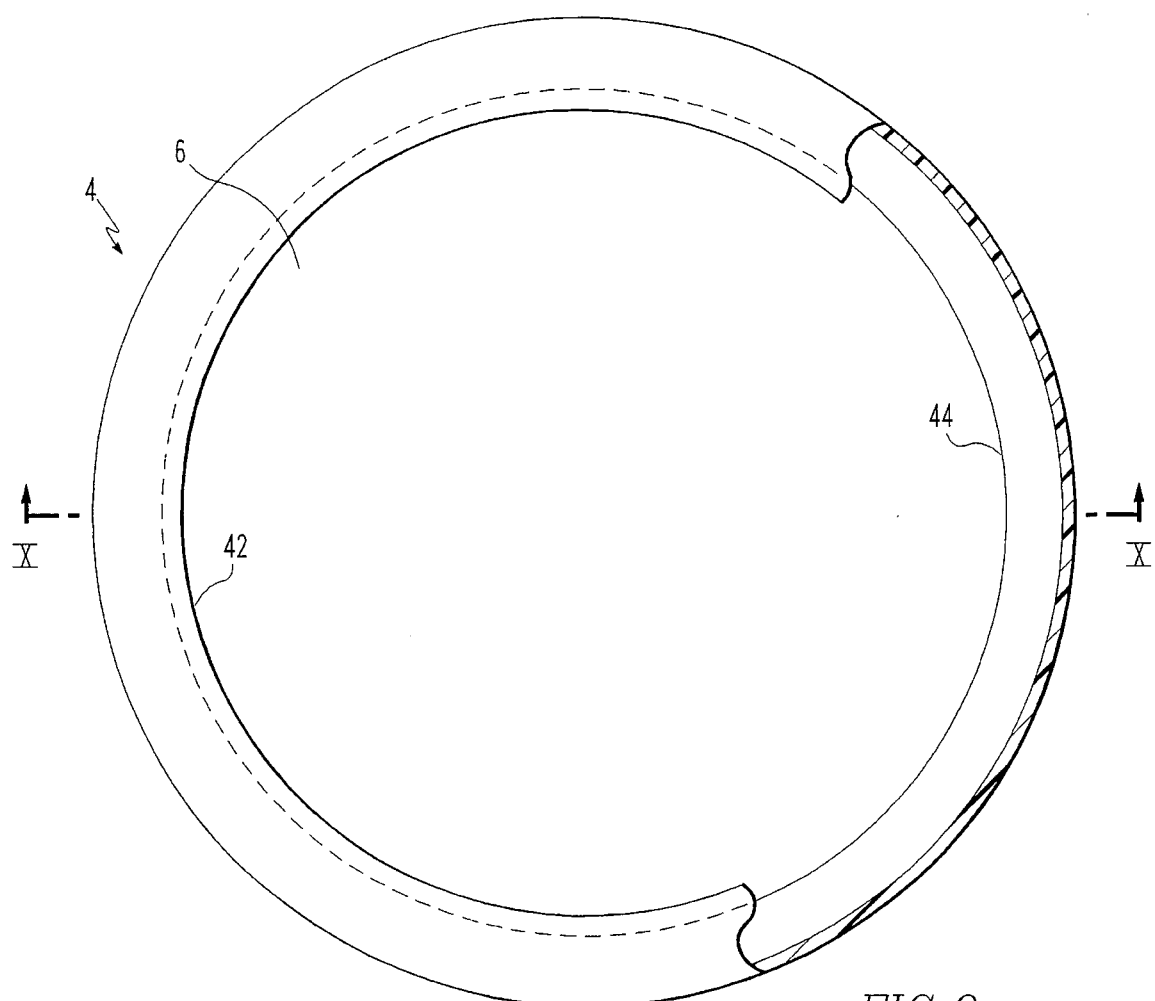
FIG. 9 is a top view, partially broken away, of another embodiment of a culture plate base in accordance with the present invention.
Figure 10:
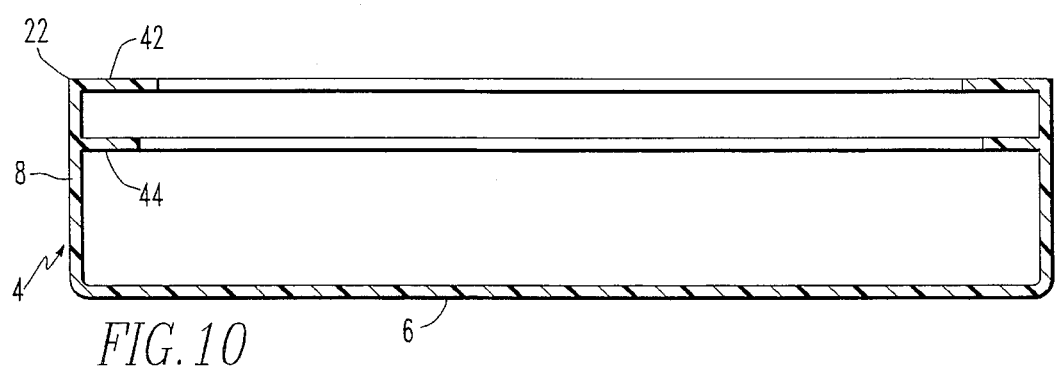
FIG. 10 is a section taken along lines X—X in FIG. 9.

The embodiment of the culture plate 32 shown in FIGS. 5 and 6 includes the splash guard attached to the lid 10. Similar to the embodiment shown in FIGS. 1–3, the culture plate 32 includes a base 4 with a bottom wall 6 and a sidewall 8 and a lid 10 with a top wall 12 and a skirt 14. In this embodiment, the splash guard is a flat, angled baffle 34, similar to the baffle 24 shown in FIGS. 1–4, and has a mounting flange 36 integral therewith and extending about the outer edge of the baffle 34. The baffle 34 is attached to the inner surface of the lid top wall 12 by the mounting flange 36. When the lid 10 is positioned on the base 4, as shown in FIG. 6, the baffle 34 extends partially inwardly and downwardly into the inner area of the base 4 at an angle to the lid 10 and the base sidewall 8 and has an outer edge 38 which is spaced from the bottom wall 6 and sidewall 8 of the base 4. Similar to the baffle 24 shown in FIGS. 1–3, the baffle 34 shown in FIGS. 5 and 6 directs flows of liquid in the base 4 away from the top edge 22 of the base sidewall 8 and back into the base 4, in the same manner as was discussed above in connection with FIG. 4.

The remaining figures show various other embodiments of a splash guard in the form of a baffle which is either formed integral with, is attached to, or is positioned within a culture plate base. The base may be the standard base discussed above in connection with FIGS. 1–6, or may be modified or specially formed to accept and hold the splash guard, or may be formed or manufactured initially to define the splash guard.

The embodiments of a culture plate base with a splash guard in accordance with the present invention shown in FIGS. 7–12 are examples of bases which are formed initially to include a splash guard. In the embodiment shown in FIGS. 7 and 8, the sidewall 8 of the base 4 is formed as a separate element from its bottom 6. The sidewall 8 and the bottom 6 are joined together by known techniques to form the complete base 4. In this embodiment, the angled baffle 24 is formed integral with the sidewall 8 and the connection between the sidewall 8 and the baffle 24 is a curved transition region 40 therebetween. In the embodiment shown in FIGS. 9 and 10, the entire base 4, including the sidewall 8, bottom 6 and splash guard, is formed as one integral unit. In this embodiment, the splash guard includes a flat top baffle 42 extending outwardly near the top edge 22 of the sidewall 8 at about a 90° angle. The splash guard also includes a flat bottom baffle 44 extending outwardly from the sidewall 8, also at about a 90° angle, and located beneath and spaced from the top baffle 42 and located above and spaced from the bottom wall 6 of the base 4. It is preferred that the top baffle 42 be somewhat wider than the bottom baffle 44 as shown. In the embodiment shown in FIGS. 11 and 12, the top baffle 46 and bottom baffle 48, extending at about 90° to the base sidewall 8, are formed by curved, molded areas in the sidewall 8. Similar to the embodiment shown in FIGS. 9 and 10, the top baffle 46 is wider than the bottom baffle 48, both baffles 46, 48 extend at about 90° to the upright sidewall 8, and the bottom baffle 48 is spaced from both the top baffle 46 and from the bottom wall 6 of the base 4.

In the embodiments shown in FIGS. 13–16, the splash guard is an annular, ring-shaped baffle which is inserted into a modified culture plate base. In the FIG. 13 and FIG. 14 embodiments, the sidewall 8 of the base 4 has a circumferential notch 50 cut therein and extending along the inner surface of the sidewall 8. The notch 50 extends parallel to and spaced above the bottom wall 6 and spaced below and parallel to the top edge 22 of the base sidewall 8. The baffle is snapped into the notch 50 in the sidewall 8, with its outer edge fully within the notch 50, to hold the baffle in place within the base 4. In the embodiment shown in FIG. 13, the baffle 52 is substantially flat and extends at about a 90° angle to the sidewall 8. In the embodiment shown in FIG. 14, the baffle 54 is angled downwardly and inwardly toward the bottom wall 6 of the base 4. In the FIG. 15 and FIG. 16 embodiments, the base 4 has a circumferential notch molded into the sidewall 8 to receive the baffle. In the FIG. 15 embodiment, the notch 56 extends substantially parallel to and spaced from the bottom wall 6 and top edge 22 of the base 4. The baffle 58 includes a flat mounting flange 60 extending along an outer edge which snaps into the notch 56 to hold the baffle 58 within the base 4. The FIG. 16 embodiment is similar to the FIG. 15 embodiment, except that the notch 62 and the mounting flange 64 on the baffle 66 are each angled outward and downward for a more secure fit of the baffle 66 within the base 4.

Figure 17:
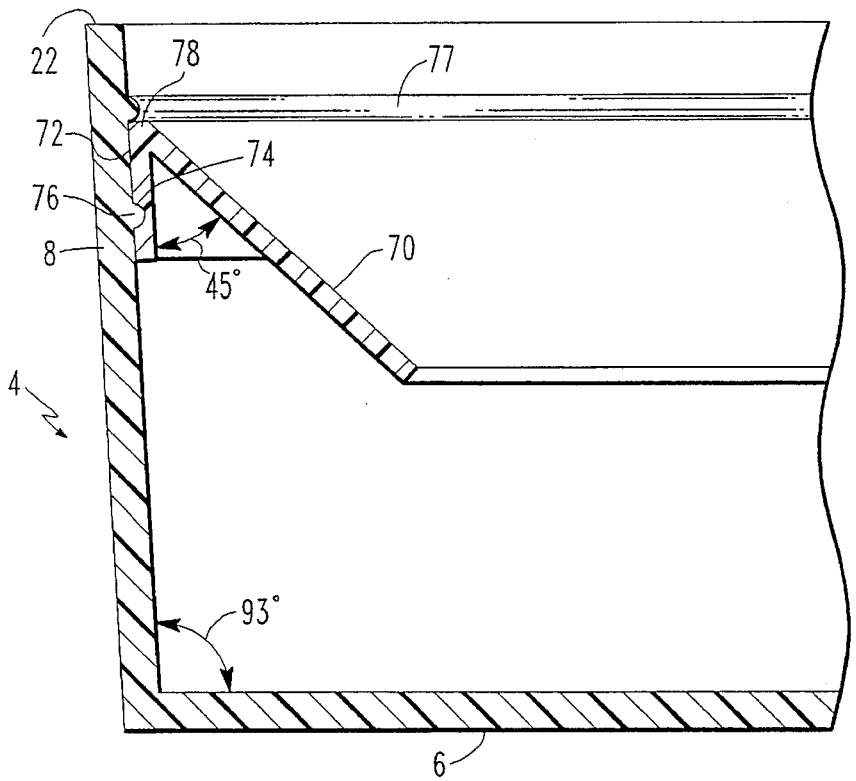
FIG. 17 is an enlarged sectional view of one side of another embodiment of a culture plate base in accordance with the present invention and showing a splash guard inserted into the base.
Figure 18:
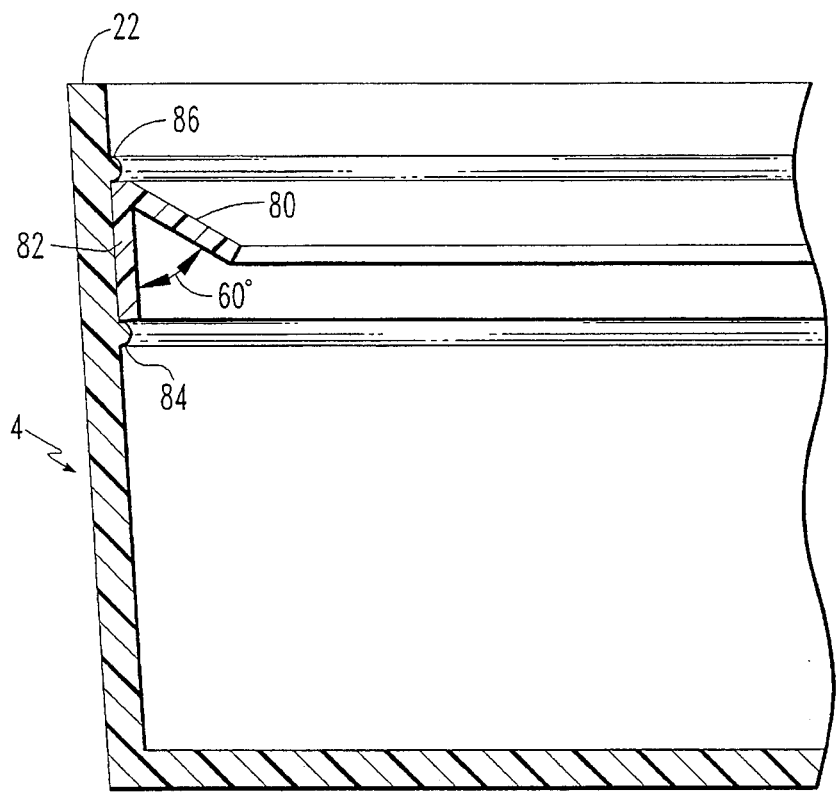
FIG. 18 is an enlarged sectional view of one side of another embodiment of a culture plate base in accordance with the present invention and showing a splash guard inserted into the base.
Figure 19:
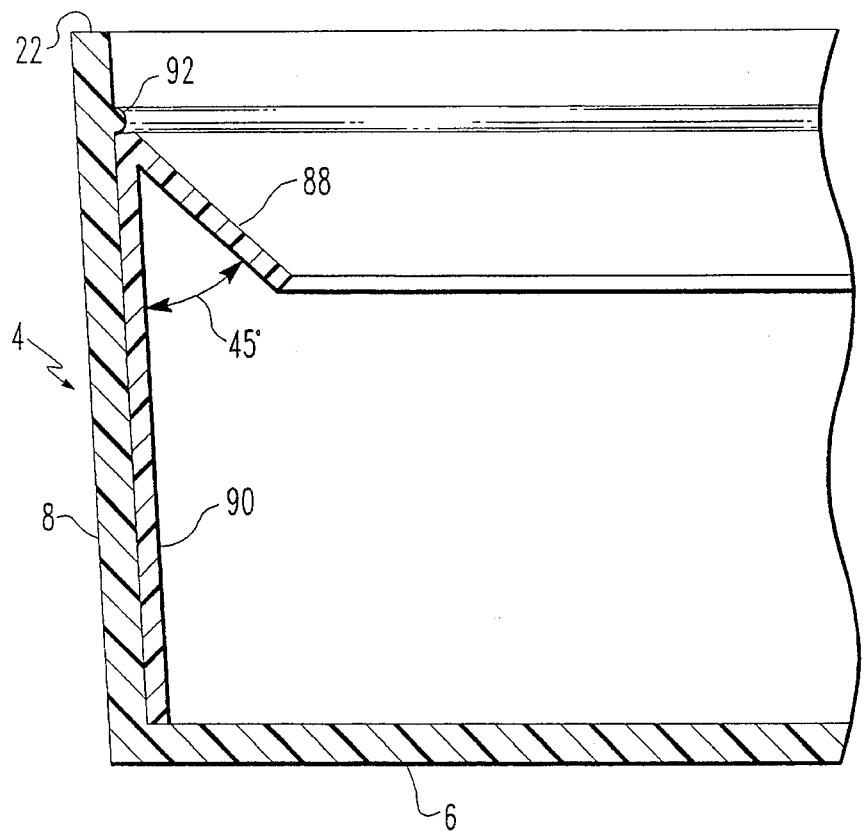
FIG. 19 is an enlarged sectional view of one side of another embodiment of a culture plate base in accordance with the present invention and showing a splash guard inserted into the base.

FIGS. 17–19 show several embodiments of a splash guard insert which can be positioned within and attached to the interior of a specially designed culture plate base. The design of the base and splash guard insert are complementary and function to hold the insert in place within the base.

In each of these embodiments, the splash guard insert includes a downwardly and inwardly angled flat baffle similar to that disclosed above, and a downwardly oriented support leg attached to the baffle along its outer edge. In the FIG. 17 embodiment, the splash guard insert includes an elongated baffle 70 attached to a shorter support leg 72 which contacts the inner surface of the sidewall 8. The outer surface of the support leg 72 includes a circumferential locking recess 74, which mates with a complementary circumferential locking ridge 76 extending along the inner surface of the sidewall 8 of the base 4. The FIG. 17 embodiment also shows a similar locking ridge 77 along the inner surface of the sidewall 8 and positioned immediately above and contacting an upper edge 78 of the support leg 72 where the baffle 70 is attached thereto. The FIG. 17 embodiment also shows the baffle 70 extending at about a 45° angle to the support leg 72 and having a length substantially longer than that of the support leg 72. The FIG. 18 embodiment shows a substantially shorter baffle 80, extending at about a 60° angle to the support leg 82. In addition, the support leg 82 has no locking recess, but is surrounded on its upper and lower edges by locking ridges 84 and 86 on the inner surface of the sidewall 8 of the base 4. In each of the FIG. 17 and FIG. 18 embodiments, the lower edge of the support leg and the outer edge of the baffle are spaced above the bottom wall 6 of the base 4, and the upper edge of the support leg is spaced below the upper edge 22 of the base. In the FIG. 19 embodiment, the baffle 88 extends from the support leg 90 at about a 45° angle and the support leg 90 extends down to and sits on the upper surface of the bottom wall 6 of the base 4. A locking ridge 92 is provided immediately above the top edge of the support leg 90 and below the top edge 22 of the base 4 to hold the splash guard insert securely in place within the base 4. The baffle 88 in the FIG. 19 embodiment is substantially shorter than the baffle 70 in the FIG. 17 embodiment, but it likewise has an outer edge that is spaced from the bottom wall 6.

Figure 20:
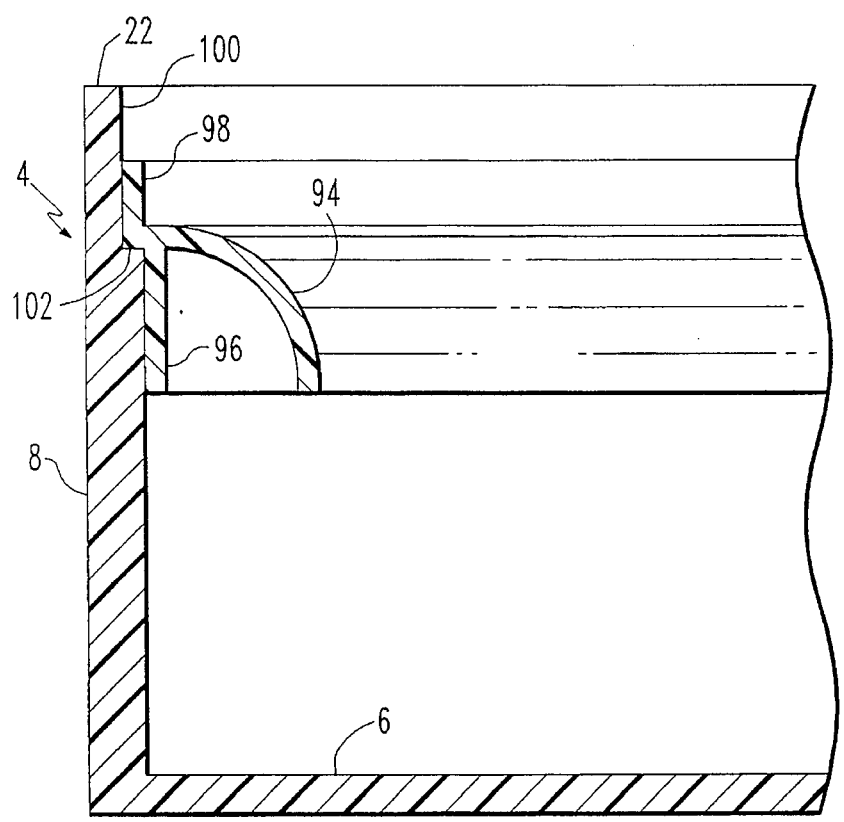
FIG. 20 is an enlarged sectional view of one side of another embodiment of a culture plate base in accordance with the present invention and showing a splash guard inserted into the base.

The FIG. 20 embodiment of a splash guard insert is similar in many aspects to the splash guard inserts shown in FIGS. 17–19. The splash guard insert includes a baffle 94 attached to a support leg 96 which contacts the inner surface of the base sidewall 8. The baffle 94 is curved, but likewise extends inwardly and downwardly and functions like the baffles discussed above. The splash guard in FIG. 20 also includes a support arm 98 which extends upwardly from an outer edge of the baffle 94 and is offset slightly outward from the support leg 96 located therebeneath. The sidewall 8 has a narrow offset 100 extending beneath its top edge 22, which forms a support shoulder 102 for the splash guard insert. The support arm 98 of the splash guard insert sits in the shoulder 102, with the support arm 98 adjacent and contacting an upper portion of the sidewall 8 and with the support leg 96 adjacent and contacting a lower portion of the sidewall 8. The lower edge of the support leg 96 is preferably spaced above the base bottom wall 6 as shown.

Figure 21:
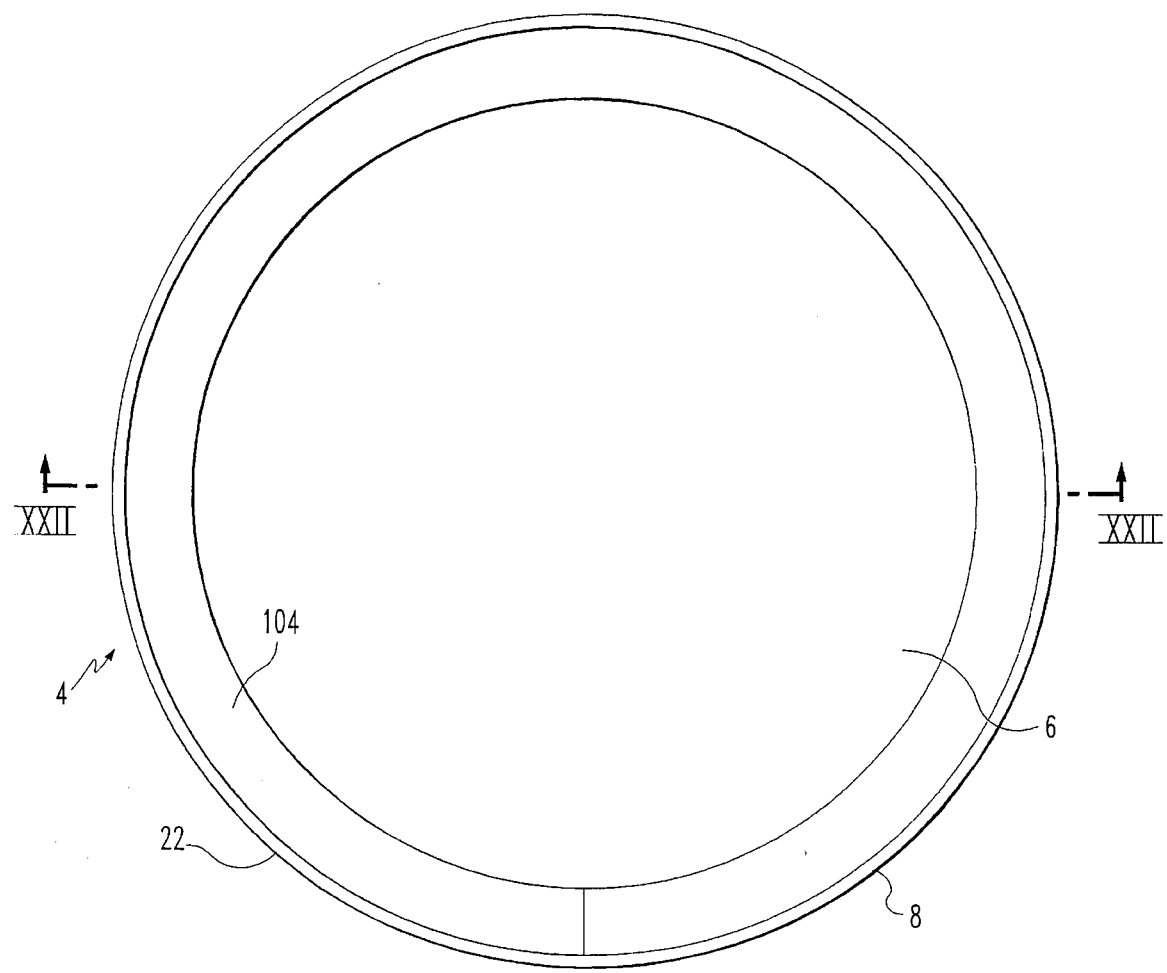
FIG. 21 is a top view of another embodiment of a culture plate base in accordance with the present invention.
Figure 22:
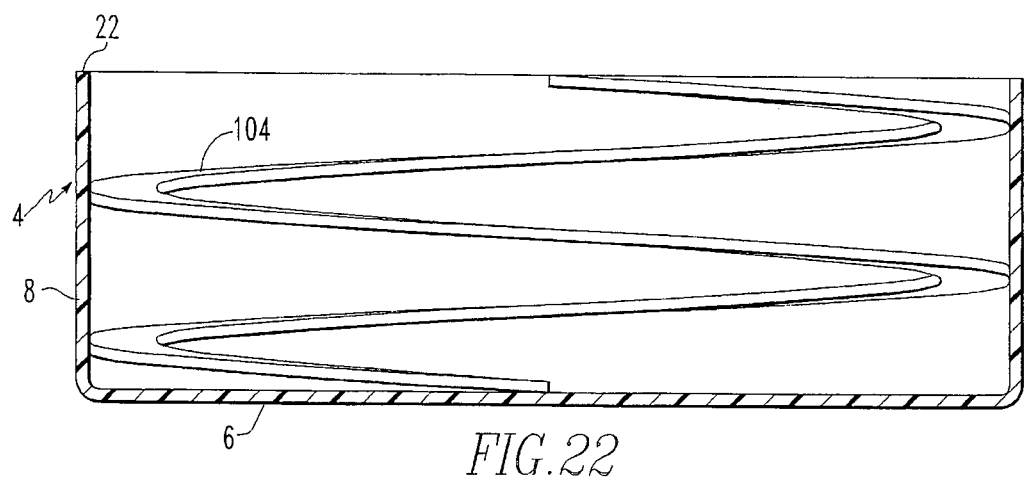
FIG. 22 is a section taken along lines XXII—XXII in FIG. 21.

FIGS. 21 and 22 show a culture plate base 4 having a flat, helical or a spiral-shaped baffle 104 positioned therein. This baffle 104 extends substantially from the bottom wall 6, along and attached to the inner surface of the sidewall 8 and to the top edge 22 of the sidewall 8.

Figure 23:
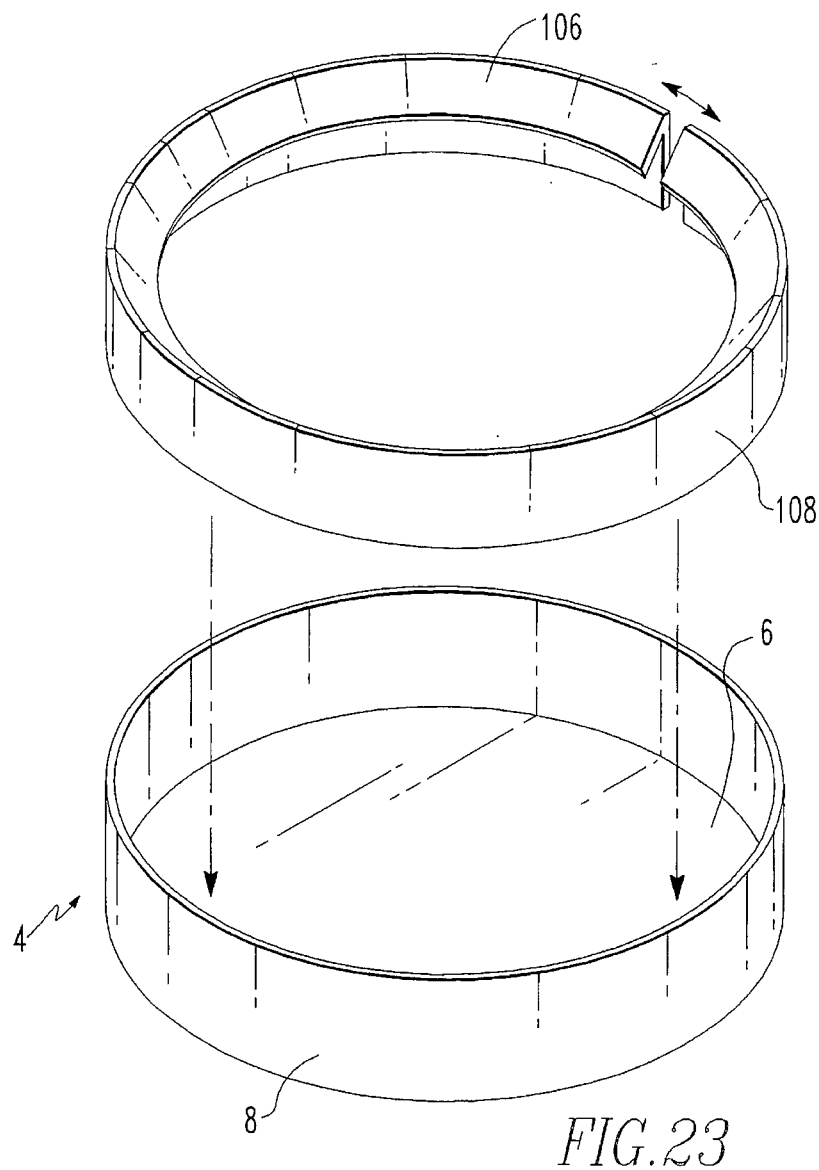
FIG. 23 is a perspective view of one embodiment of a splash guard insert in accordance with the present invention being inserted into a standard culture plate base.
Figure 24:
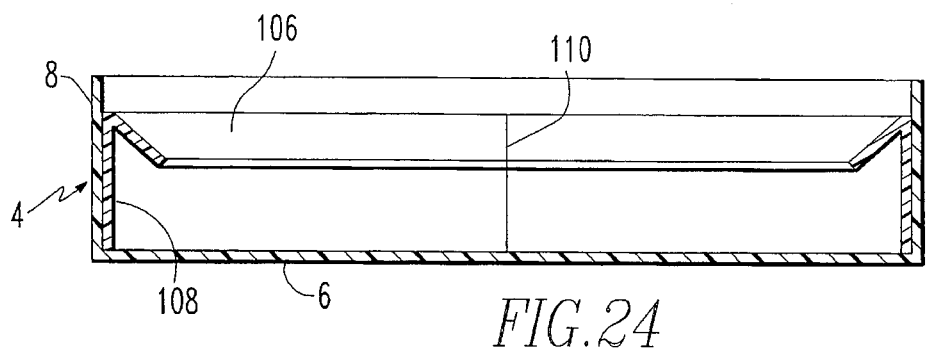
FIG. 24 is a section taken through the culture plate base shown in FIG. 23, with the splash guard insert in place.

FIGS. 23–28 show splash guards which can be inserted into the base of a standard culture plate without modification to the base. In the embodiment shown in FIGS. 23 and 24, the splash guard insert is similar to that shown in FIG. 19 above. The splash guard insert is a ring-shaped structure including an angled baffle 106 and a support leg 108 connected thereto which extends downwardly to and sits upon the upper surface of the bottom wall 6 when the splash guard is positioned within the base 4. While this splash guard could be formed as a solid ring-shaped element, it can also be formed, as shown, of an elongated, extruded member which is bent to form the ring shape. This is shown more clearly in FIG. 23 which shows the splash guard being inserted into the culture plate base 4. Due to the inherent tendency of an extruded member to regain its initial shape, the extruded splash guard insert formed into a circular shape will exert force against the inner surface of the sidewall 8 and remain securely in place. Reference number 110 in FIG. 24 shows where the ends of the extruded member abut each other when the splash guard insert is in place within the base 4.

Figure 25:
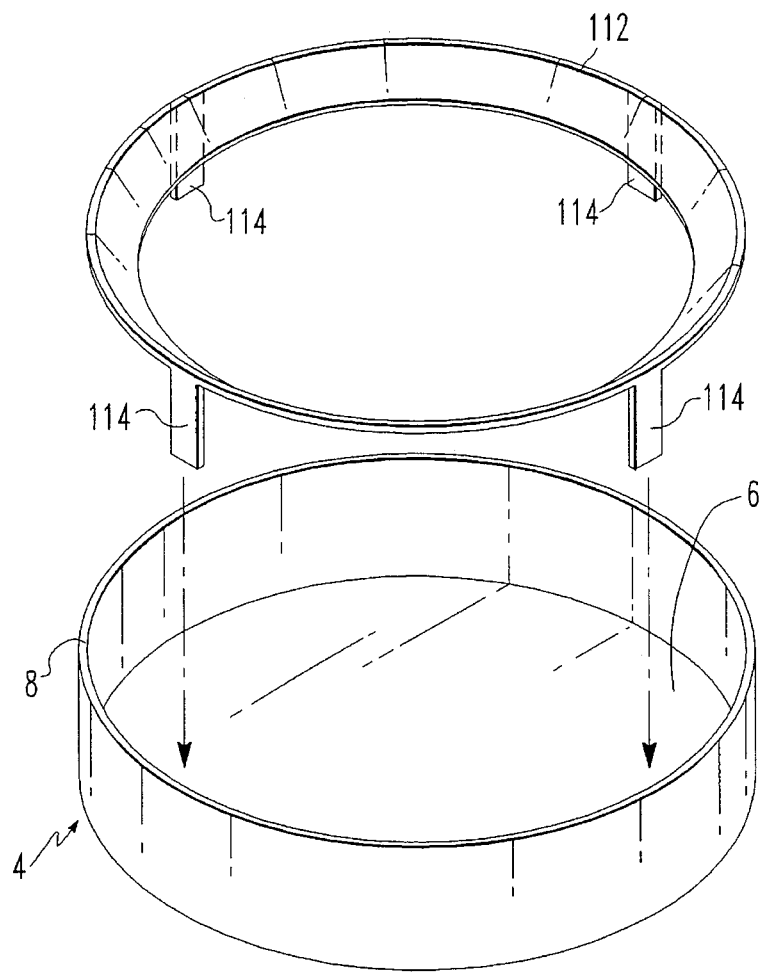
FIG. 25 is a perspective view of another embodiment of a splash guard insert in accordance with the present invention being inserted into a standard culture plate base.
Figure 26:
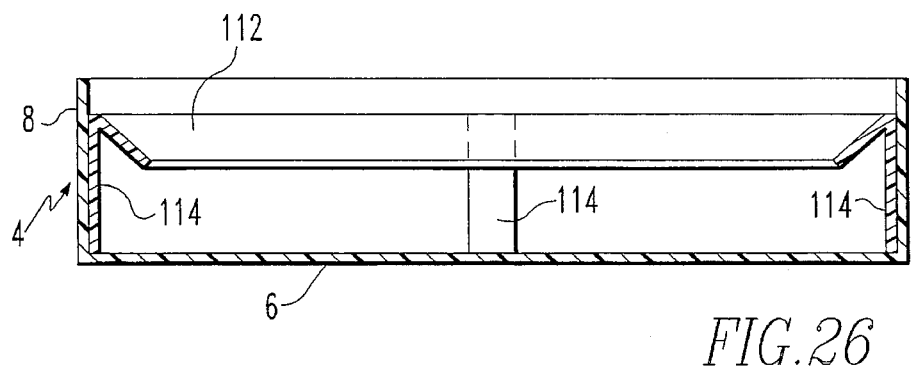
FIG. 26 is a section taken through the culture plate base shown in FIG. 25, with the splash guard insert in place.

The splash guard embodiment shown in FIGS. 25 and 26 is also an insert for a standard culture plate base 4. This splash guard includes a continuous, angled baffle 112 with a plurality of spaced, separate support legs 114 extending downwardly from and attached to the baffle 112. The support legs 114 are preferably spaced evenly about the baffle 112 and in sufficient numbers to hold the baffle 112 above the bottom wall 6 of the base 4. In the area of the support legs, this splash guard has much the same cross-sectional shape as that shown in FIG. 24. However, the FIGS. 25 and 26 splash guard is lighter and uses less material since the support legs 114 are positioned only in several locations along the baffle 112, rather than the continuous, wall-like support leg 108 shown in the FIGS. 23 and 24 embodiment.

Figure 27:
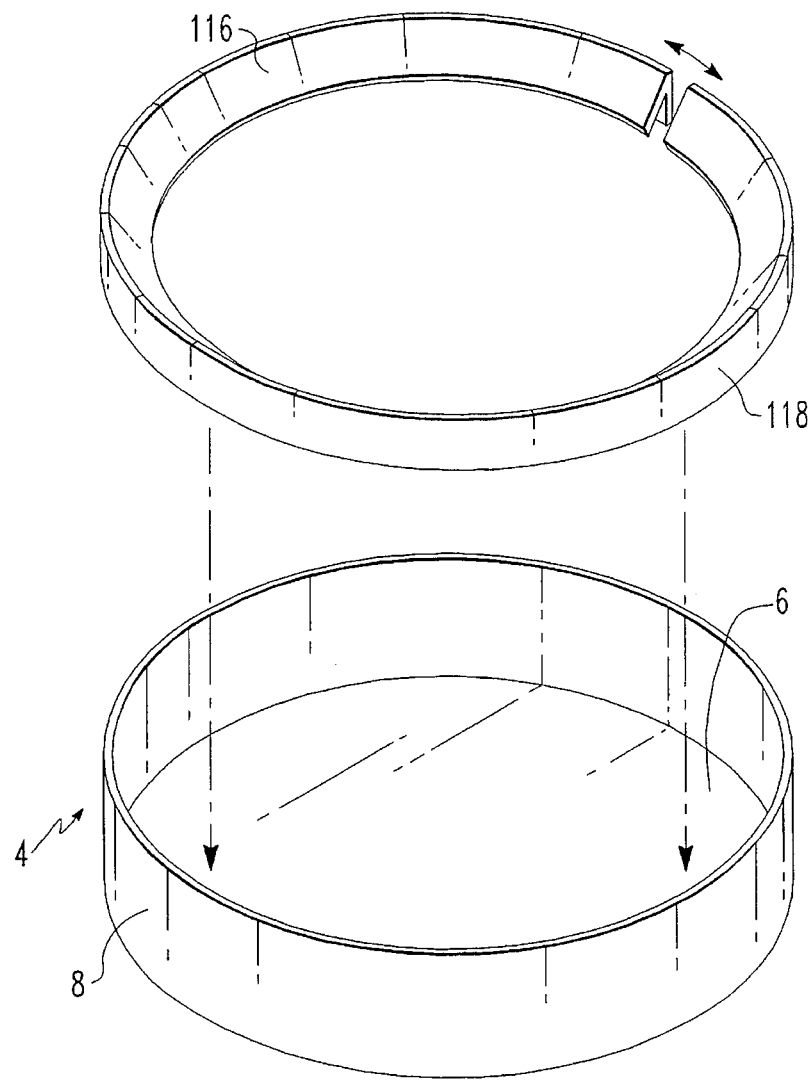
FIG. 27 is a perspective view of another embodiment of a splash guard insert in accordance with the present invention being inserted into a standard culture plate base.
Figure 28:
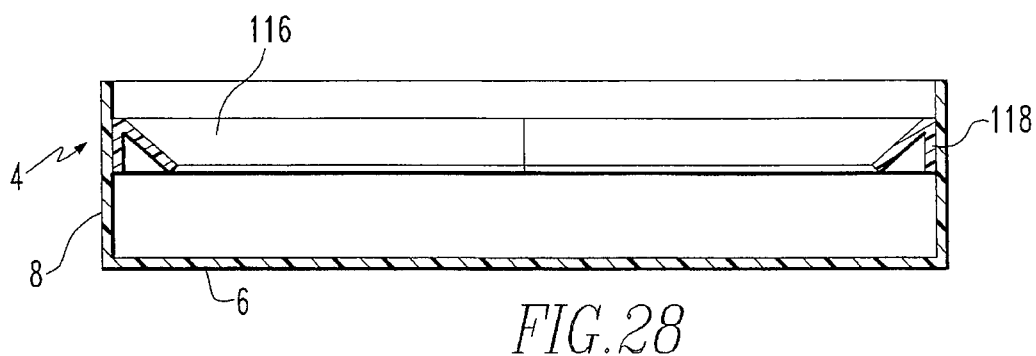
FIG. 28 is a section taken through the culture plate base shown in FIG. 27, with the splash guard insert in place.

The splash guard insert shown in FIGS. 27 and 28 is similar to the embodiment shown in FIGS. 23 and 24, with an angled baffle 116 attached to a downwardly oriented support leg 118. In addition, the splash guard shown in FIGS. 27 and 28 can be a solid member or can be an extruded member which is bent into a circular shape as shown in FIG. 27. However, unlike the FIGS. 23 and 24 embodiment, the support leg 118 in the FIGS. 27 and 28 embodiment extends downwardly along only a portion of the base sidewall 8. The support leg 118 stops short of and is spaced above the bottom wall 8 as shown in FIG. 28. In this embodiment, the tension of the bent, extruded splash guard exerted against the inner surface of the sidewall 8 should be sufficient to hold the splash guard insert in place. However, it would be preferred that this splash guard be securely affixed to the inner surface of the sidewall 8 by adhesives or the like, particularly if the splash guard insert is formed initially in a ring shape.

Figure 29:
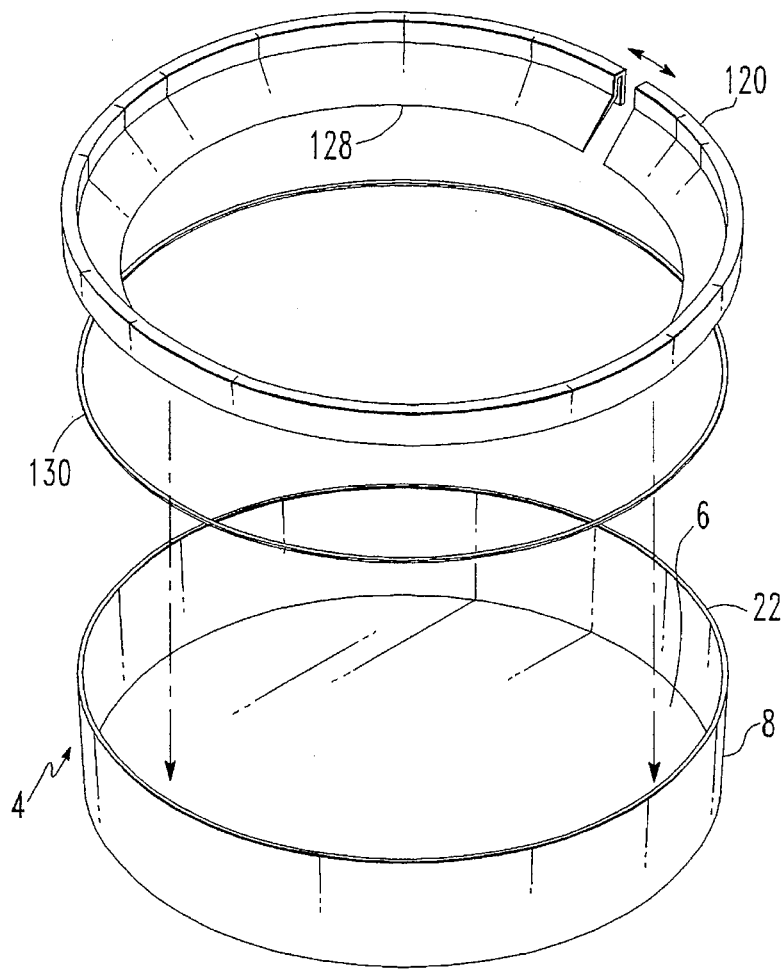
FIG. 29 is a perspective view of a splash guard attachment in accordance with the present invention being attached to a standard culture plate base.
Figure 30:
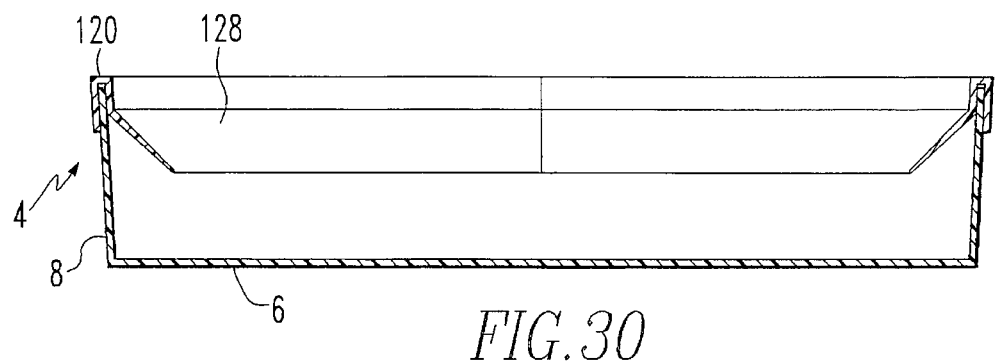
FIG. 30 is a section taken through the culture plate base shown in FIG. 29, with the splash guard attachment in place.
Figure 31:
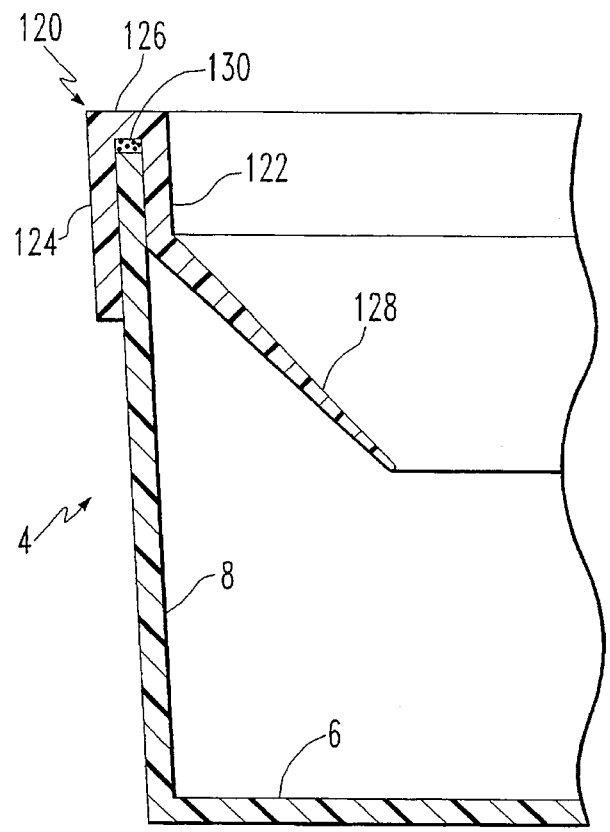
FIG. 31 is an enlarged sectional view of one side of the culture plate base with attached splash guard shown in FIG. 30.
Figure 32:
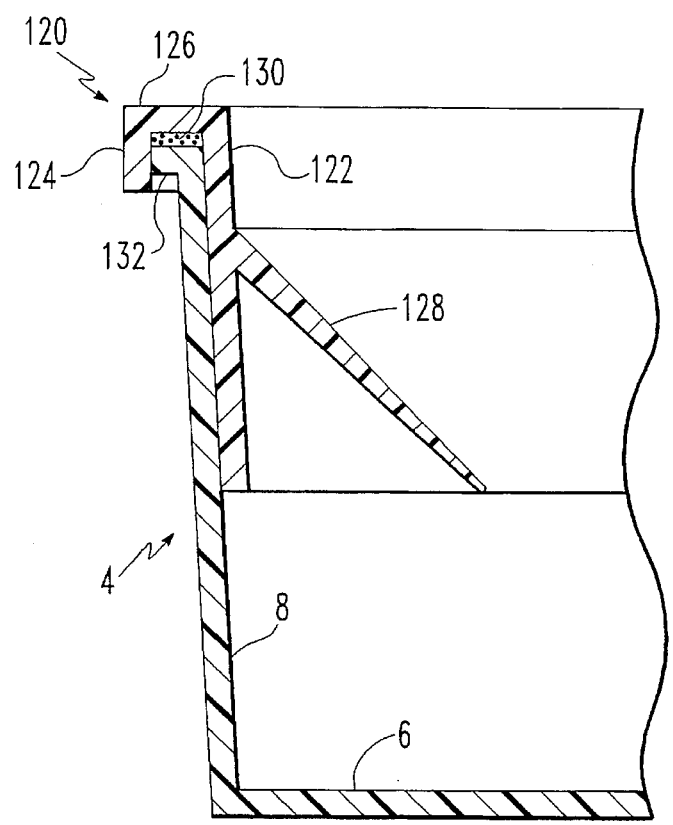
FIG. 32 is an enlarged sectional view, similar to FIG. 31, of one side of another embodiment of a culture plate base with another embodiment of a splash guard attachment in accordance with the present invention attached thereto.

FIGS. 29–32 show a splash guard which is attached to the base 4 of a standard culture plate by hanging the splash guard on the sidewall 8 along its top edge 22. This splash guard includes an inverted U-shaped support bracket 120 which is configured to straddle the top edge 22 and securely contact both the inner and outer surfaces of the base sidewall 8. The support bracket 120 includes an inner member 122 and outer member 124 joined by top member 126. An angled baffle 128 is attached along its outer edge to the inner member 122 of the support bracket 120. A ring-shaped gasket or seal or adhesive member 130 can be positioned between the top edge 22 of the sidewall 8 and the support bracket 120, beneath the top member 126, to hold the splash guard in place. The gasket 130 can be die cut or the like and made from silicone, close cell urethane or other foams. The baffle 128 can be connected to the lower edge of the inner member 122 of the support bracket 120 as shown in FIGS. 29–31 or can be connected to a middle area of the inner member 122 of the support bracket 120 as shown in FIG. 32. The FIG. 32 embodiment has a longer length of the inner member 122 contacting the sidewall 8 and may provide a more stable and secure fit than the FIGS. 29–31 embodiment. As shown in FIG. 32, if the top edge 22 of the sidewall 8 of the base 4 has a flange 132 or the like, the support bracket 120 can be configured to accommodate this element. The hang-on splash guard shown in FIGS. 29 and 30 is formed as an extruded member similar to the splash guard insert shown in FIGS. 23, 24, 27 and 28. While an extruded construction is preferred, the hang-on splash guard can also be formed as a solid, ring-shaped element.

Figure 15:
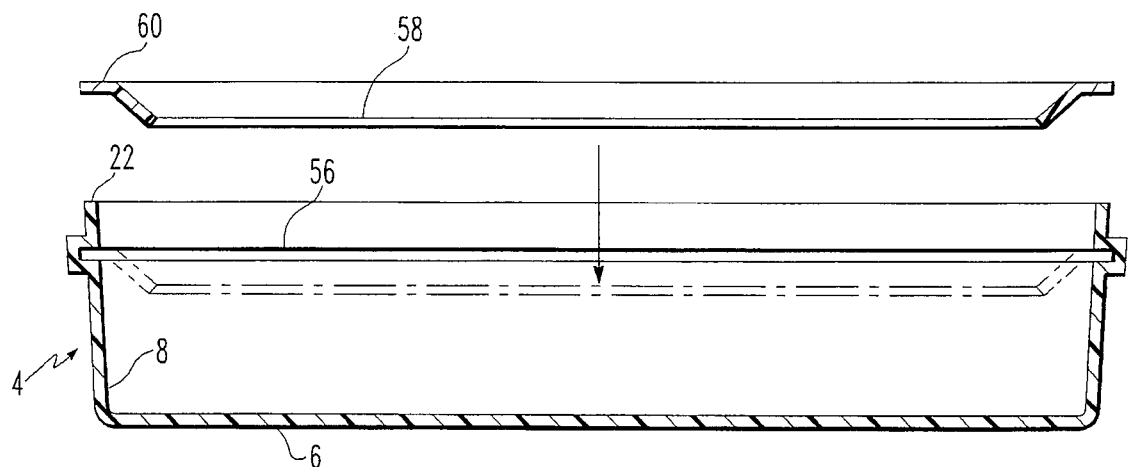
FIG. 15 is a section taken through another embodiment of a culture plate base in accordance with the present invention and showing a splash guard being inserted into the base.
Figure 16:
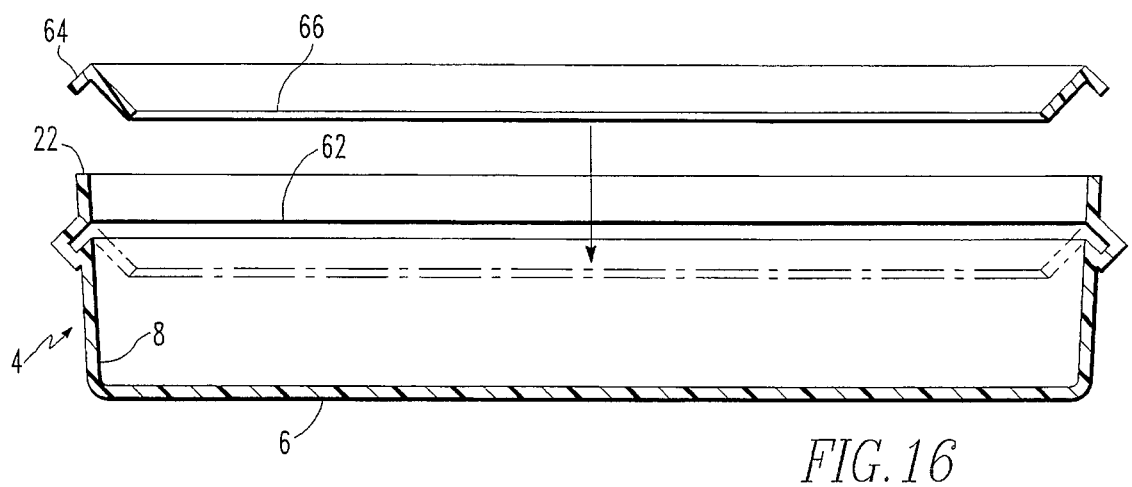
FIG. 16 is a section taken through another embodiment of a culture plate base in accordance with the present invention and showing a splash guard being inserted into the base.
Figure 33:
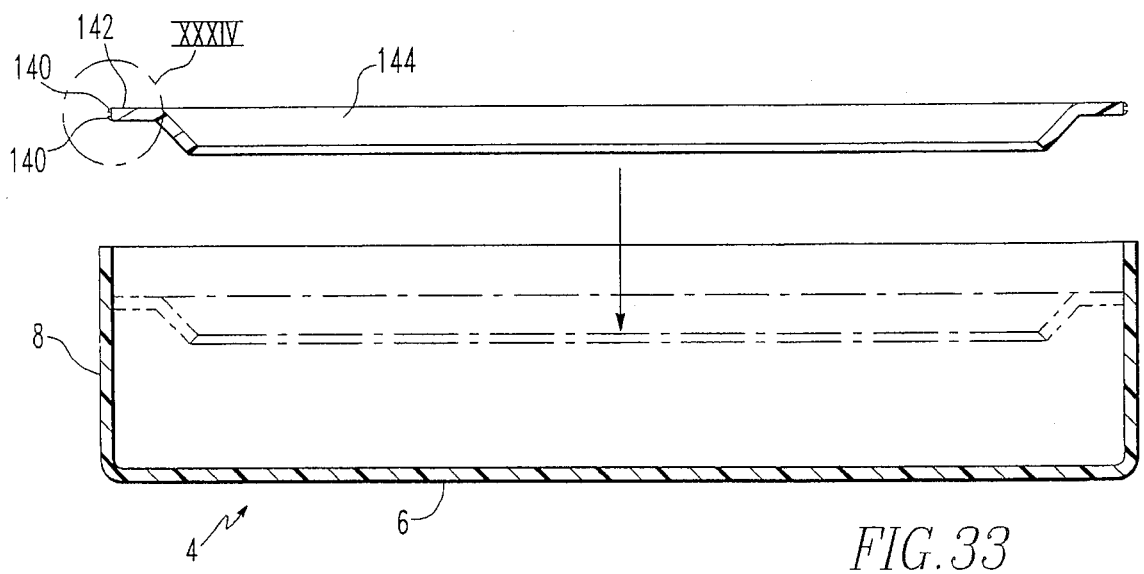
FIG. 33 is a section taken through another embodiment of a splash guard insert in accordance with the present invention being inserted into a standard culture plate base.
Figure 34:
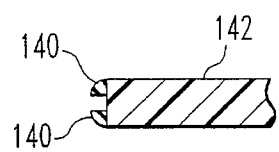
FIG. 34 is an enlarged sectional view of an outer portion of the splash guard insert shown in FIG. 33.
Figure 35:
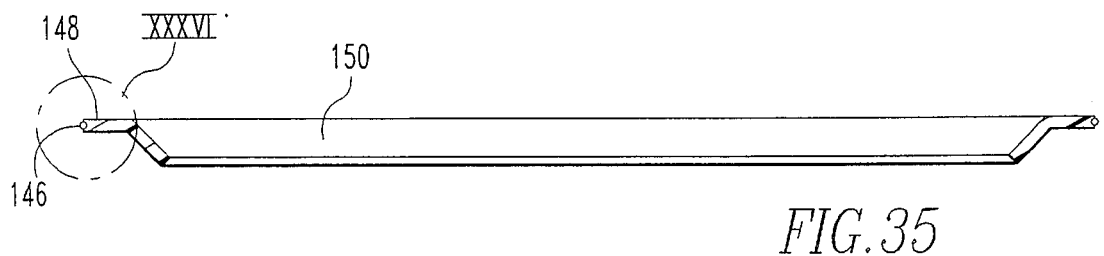
FIG. 35 is a section through another embodiment of a splash guard insert in accordance with the present invention.
Figure 36:
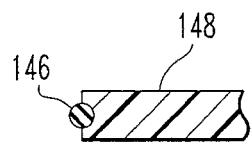
FIG. 36 is an enlarged sectional view of an outer portion of the splash guard insert shown in FIG. 35.

FIGS. 33–36 show another arrangement for a splash guard which can be inserted into the base of a standard culture plate. In this arrangement, an annular, ring-shaped baffle, such as one similar to that shown in FIG. 15, is provided with a frictional engagement member along its outer peripheral edge. Through the use of this frictional engagement member, the baffle can be positioned within the base at any desired height and held in place without the need for special modifications to the sidewall 8 of the base 4. In the embodiment shown in FIGS. 33 and 34, a double gasket 140 is provided along the outer peripheral edge of a mounting flange 142 attached to the baffle 144. In the embodiment shown in FIGS. 35 and 36, an O-ring 146 is provided along the outer peripheral edge of a mounting flange 148 attached to the baffle 150. By merely pushing the splash guard into the base 4, as shown in FIG. 33, the frictional engagement member (double gasket 140 or O-ring 146 or the like) contacts the inner surface of the sidewall 8 and holds the splash guard (baffle and mounting flange) securely in place. The double gasket 140 or O-ring 146 can be made from a urethane or silicone material.

Figure 37:
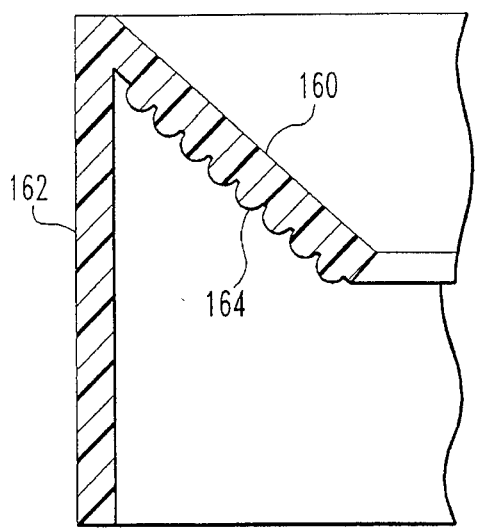
FIG. 37 is a section through an outer portion of another embodiment of a splash guard insert in accordance with the present invention.
Figure 38:
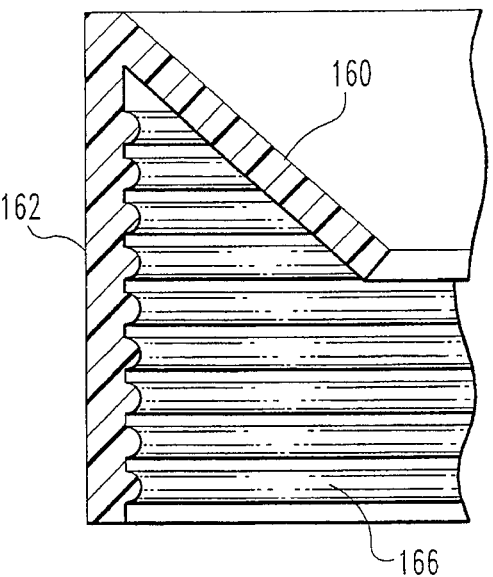
FIG. 38 is a section through an outer portion of another embodiment of a splash guard insert in accordance with the present invention.
Figure 39:
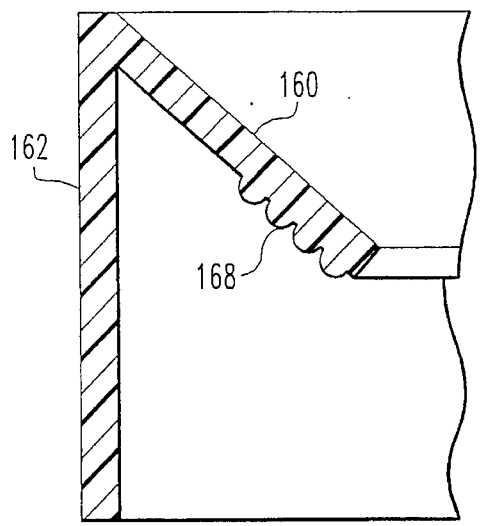
FIG. 39 is a section through an outer portion of another embodiment of a splash guard insert in accordance with the present invention.
Figure 40:
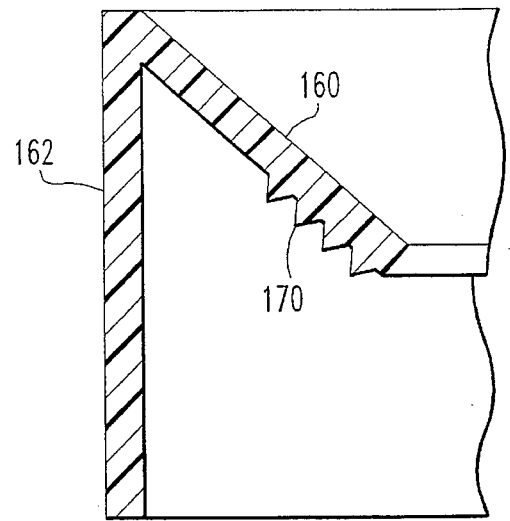
FIG. 40 is a section through an outer portion of another embodiment of a splash guard insert in accordance with the present invention.

FIGS. 37–40 show additional modifications which can be made to the splash guard of the present invention, whether included in a baffle integral, an insert, or a hang-on arrangement. Corrugations or other irregularities can be provided on the inner, liquid facing surfaces of the splash guard to diffuse and break up fluid flows therealong. These features provide a damping action which slows the fluid flows and helps ensure that the fluids remain within the base. For clarity sake, FIGS. 37–40 show a splash guard including a baffle 160 and a support leg 162 attached thereto. FIG. 37 shows rounded corrugations 164 provided on an inner surface of the baffle 160 along its entire length. FIG. 38 shows rounded corrugations 166 provided along the inner surface of the support leg 162 along its entire length. FIG. 39 shows rounded corrugations 168 provided along a portion of the inner surface of the baffle 160 near its inner edge. FIG. 40 shows an arrangement similar to that in FIG. 39, but with a pointed corrugation 170 on the baffle 160, rather than rounded corrugations. The corrugations or other surface irregularities can be provided on one or both of the baffle 160 and support leg 162, along all or a portion of the length of their inner surfaces.

Figure 11:
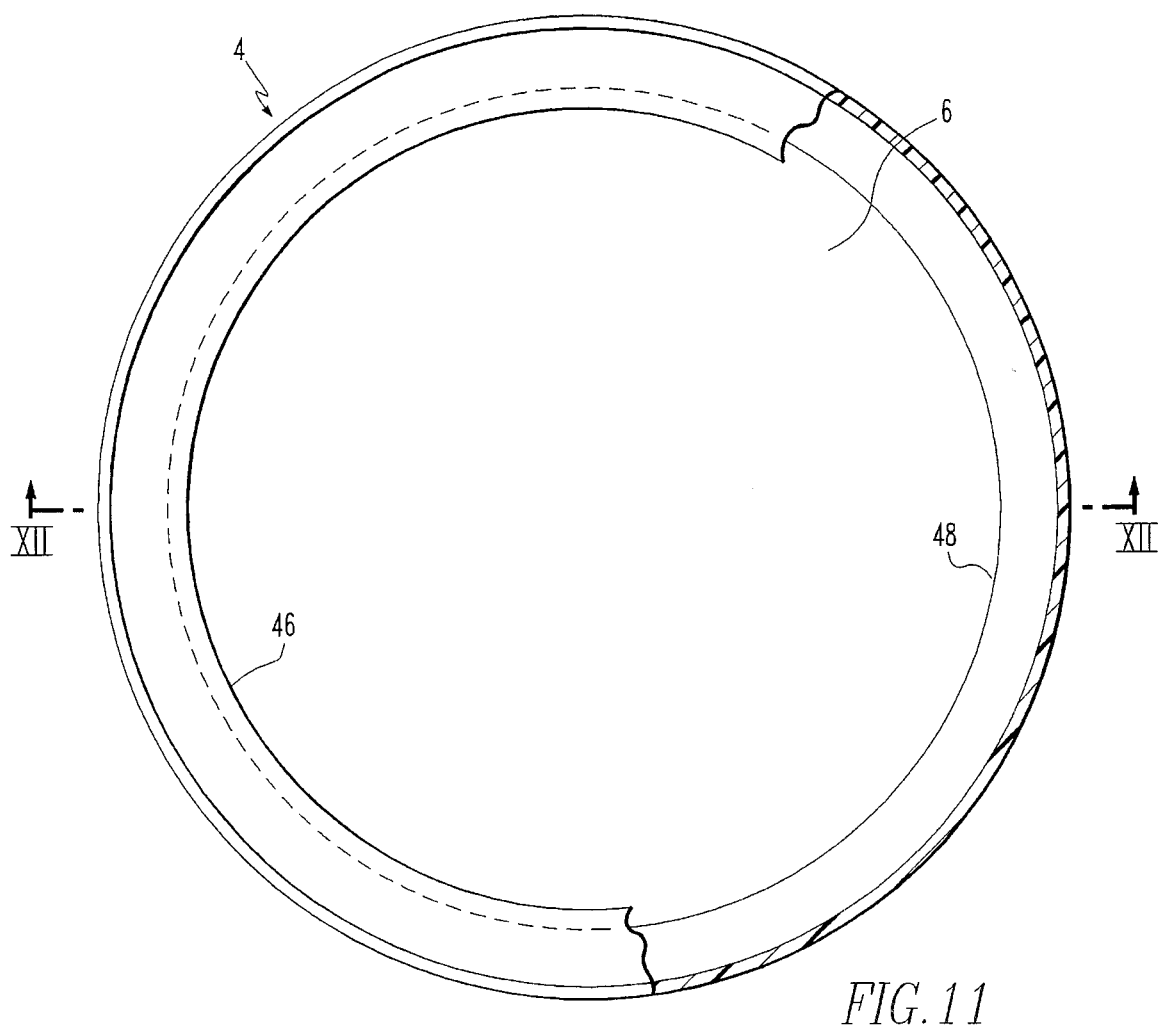
FIG. 11 is a top view, partially broken away, of another embodiment of a culture plate base in accordance with the present invention.
Figure 12:
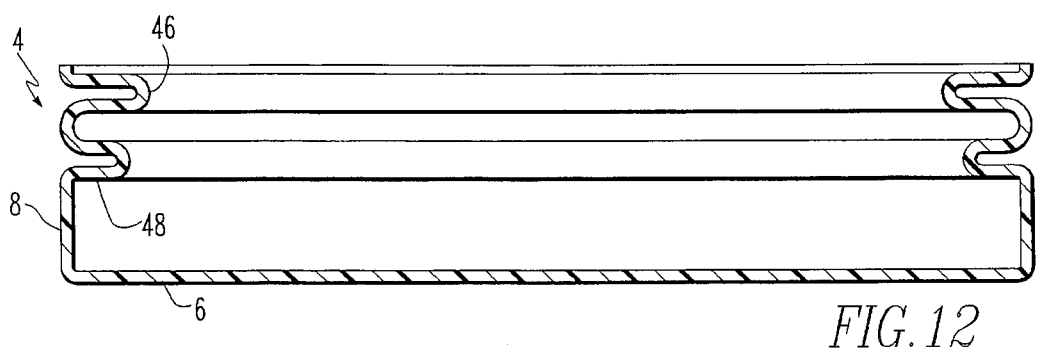
FIG. 12 is a section taken along lines XII—XII in FIG. 11.
Figure 13:
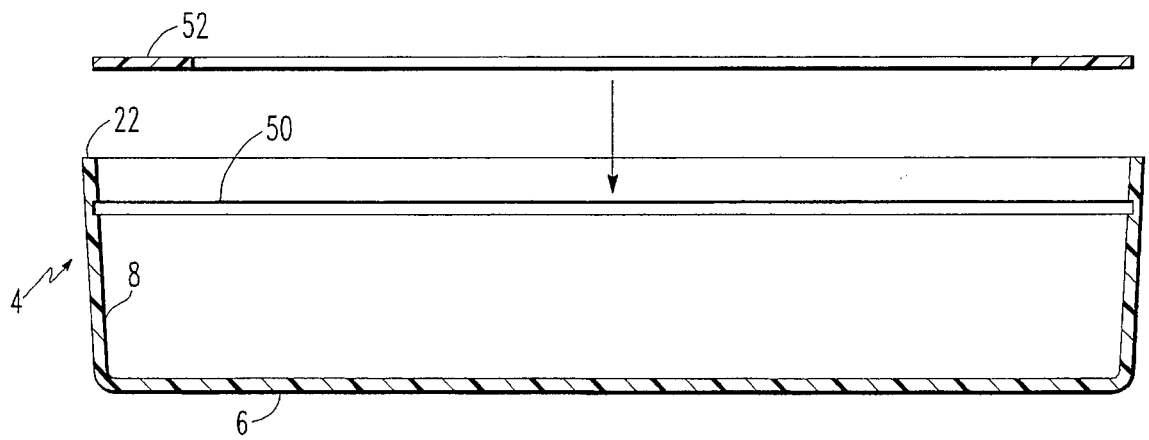
FIG. 13 is a section taken through another embodiment of a culture plate base in accordance with the present invention and showing a splash guard being inserted into the base.
Figure 14:
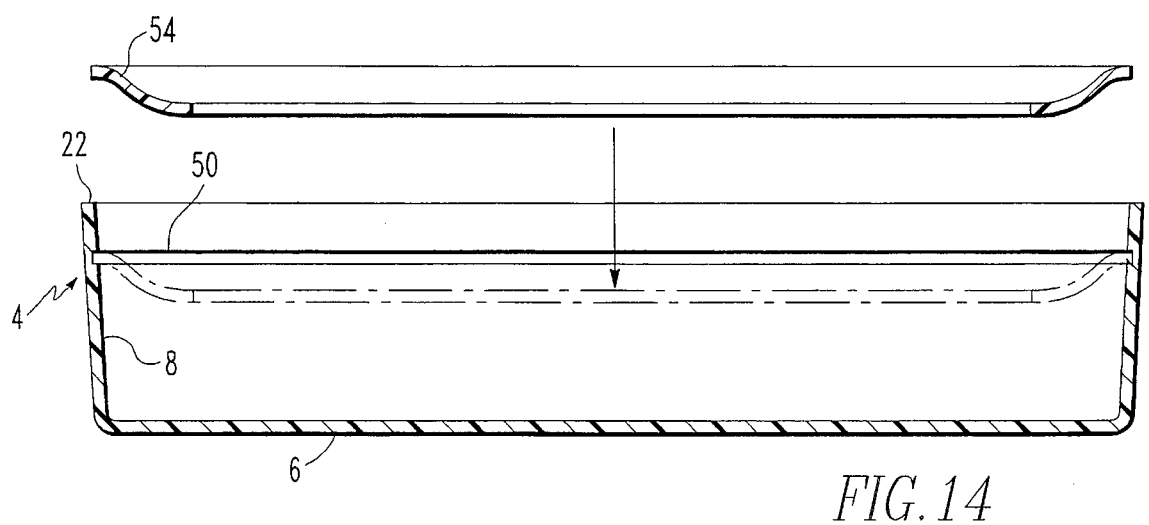
FIG. 14 is a section taken through another embodiment of a culture plate base in accordance with the present invention and showing a splash guard being inserted into the base.

The culture plate bases and lids and the various splash guards shown in the drawings and described above may be made of various available materials and utilizing various available manufacturing techniques. As one skilled in the art will readily appreciate, some materials and/or manufacturing techniques may be more appropriate for a particular design. One or more of the following materials should prove to be satisfactory: nylon, polycarbonates, crystal polystyrene, polyethylene terephthalate (PET), polyethylene terephthalate glycol (PETG), copolyesters, polyvinyl chloride (PVC), high-density polyethylene (HDPE) and urethanes. In addition, one or more of the following manufacturing techniques may be appropriate: blow molding, injection molding, compression molding, vacuum/thermo forming and extrusion. Post manufacturing and assembly operations may include mechanical assembly, spin welding, sonic welding, spot sonic welding, adhesive bonding and spot adhesive bonding. The extrusion process is appropriate for the splash guard inserts shown in FIGS. 17–32 and 37–40, but not for the other elements in these or other figures. Injection molding and compression molding are the preferred techniques for manufacturing the embodiments shown in FIGS. 9–10 and the base shown in FIGS. 13–14. Blow molding is the preferred technique for manufacturing the embodiment shown in FIGS. 11–12. Compression molding may not be appropriate for forming the base shown in FIGS. 1–4. Blow molding may not be appropriate for manufacturing the splash guards shown in FIGS. 15–30. The embodiment shown in FIGS. 9–10 and the base shown in FIGS. 13–14 are preferably made from polystyrene. The embodiment shown in FIGS. 11–12 is preferably made from PET, PETG or PVC. The standard culture plate bases are typically made from polystyrene, PET, PETG or PVC, but this is not particularly crucial. Otherwise, any of the manufacturing techniques and/or materials may be employed.

Having described above the presently preferred embodiments of the present invention, it is to be understood that the invention may be otherwise embodied within the scope of the appended claims.

I claim:

1. A culture plate comprising an open-topped base having a bottom wall and a sidewall extending upwardly from said bottom wall and attached thereto, a lid having a top wall and a skirt extending downwardly from said top wall and attached thereto, said lid configured to fit over and sit on a top edge of the base sidewall and cover an inner area enclosed by said base, and a splash guard including a baffle attached to an inner surface of said lid top wall and extending partially inward into an inner area of said base, said splash guard configured to direct liquid flows away from the top edge of said base sidewall and back into said base.

2. The culture plate of claim 1 wherein said lid and base each have a cylindrical configuration and said baffle is an annular, ring-shaped member attached along an outer edge to said lid top wall.

3. The culture plate of claim 1 wherein said baffle is attached along an outer edge to said lid top wall and, when said lid is positioned on said base, said baffle extends inwardly and downwardly at an angle to said lid and said base sidewall and said baffle has an inner edge which is spaced from the bottom wall and sidewall of said base.

4. A base for a culture plate comprising a bottom wall and a sidewall extending upwardly from said bottom wall and attached thereto to form an open-topped structure, with the width of said bottom wall being substantially larger than the height of said sidewall, and a splash guard attached to said base and extending partially inward into an inner area enclosed by said base, said splash guard configured to direct liquid flows away from a top edge of said base sidewall and back into said base, with said splash guard including a solid baffle attached to an inner surface of said base sidewall, with said base having a cylindrical configuration, with said baffle formed as an annular ring-shaped member attached along an outer edge to said base sidewall and having no liquid passages therethrough, and with said baffle extending inwardly and downwardly at an angle of between 35° and 75° to said base sidewall and having an inner edge which is spaced from the bottom wall and sidewall of said base.

5. The culture plate base of claim 4 wherein said baffle extends from said base sidewall at an angle of about 45°.

6. The culture plate base of claim 4 wherein said baffle is integral with said base sidewall.

7. The culture plate base of claim 4 wherein said baffle is removably attached to said base sidewall.

8. The culture plate base of claim 4 wherein said baffle is attached along its outer edge to a support leg which is attached to the inner surface of said base sidewall, with said support leg extending downward toward, but stopping short of, said base bottom wall.

9. The culture plate base of claim 8 wherein said support leg fits within an offset in the inner surface of said base sidewall and is supported by a shoulder formed by said offset.

10. The culture plate base of claim 9 wherein the base sidewall slopes outwardly from said base bottom wall at an angle from vertical.

11. The culture plate base of claim 9 wherein the base sidewall slopes outwardly from said base bottom wall at an angle of about 3° from vertical.

12. The culture plate base of claim 9 further including a circumferential locking ridge on the inner surface of said base sidewall immediately above said baffle.

13. A lid for a culture plate comprising a top wall and a skirt extending downwardly from said top wall and attached thereto, said lid configured to fit over and cover an open-topped culture plate base having a bottom wall and a sidewall, said lid including a splash guard attached to said lid and configured to extend partially inward into an inner area enclosed by the base, and configured to direct liquid flows away from a top edge of the base sidewall and back into the base when said lid is positioned on a base.

14. The culture plate lid of claim 13 wherein said splash guard includes a baffle attached to an inner surface of said lid top wall.

15. The culture plate lid of claim 14 wherein said lid has a cylindrical configuration and said baffle is an annular, ring-shaped member attached along an outer edge to the lid top wall.

16. The culture plate lid of claim 14 wherein said baffle is attached along an outer edge to said lid top wall and, when said lid is positioned on said base, said baffle extends inwardly and downwardly at an angle to said lid and said base sidewall and said baffle has an inner edge which is spaced from the bottom wall and sidewall of said base.

17. A base for a culture plate comprising a bottom wall and a sidewall extending upwardly from said bottom wall and attached thereto to form an open-topped structure and a splash guard attached to said base and extending partially inward into an inner area enclosed by said base, with said splash guard configured to direct liquid flows away from a top edge of said base sidewall and back into said base, with said splash guard including a pair of spaced baffles attached to an inner surface of said base sidewall and extending inwardly at an angle of about 90° to said base sidewall, and with an upper baffle of said pair of baffles being wider than a lower baffle of said pair of baffles.

18. A base for a culture plate comprising a bottom wall and a sidewall extending upwardly from said bottom wall and attached thereto to form an open-topped structure and a splash guard attached to said base and extending partially inward into an inner area enclosed by said base, with said splash guard configured to direct liquid flows away from a top edge of said base sidewall and back into said base, wherein said splash guard is an insert positioned within said base, with said splash guard including a baffle attached along its outer edge to a support leg, and with said support leg having an outer surface in contact with an inner surface of said base sidewall and having a lower edge in contact with and supported by the bottom wall of said base, with said baffle extending inwardly and downwardly at an angle to said support leg, and with said baffle having an inner edge which is spaced from said support leg and from the bottom wall of said base.

19. The culture plate base of claim 18 wherein said baffle extends from said support leg at an angle of between 35° and 75°.

20. The culture plate base of claim 18 wherein said baffle extends from said support leg at an angle of about 45°.

* * * * *